US006018042A

United States Patent [19]
Mett et al.

[11] Patent Number: 6,018,042
[45] Date of Patent: Jan. 25, 2000

[54] ANTITUMOR ANTISENSE OLIGONUCLEOTIDES

[75] Inventors: Helmut Mett, Neuenburg, Germany; Robert Häner, Fehren, Switzerland; Nicholas Mark Dean, Cardiff by the Sea, Calif.

[73] Assignee: Novartis AG, Basel, Switzerland

[21] Appl. No.: 08/914,961

[22] Filed: Aug. 20, 1997

Related U.S. Application Data

[63] Continuation of application No. 08/287,753, Aug. 9, 1994, abandoned.

[51] Int. Cl.$^7$ .................................................... C07H 21/00
[52] U.S. Cl. ........................................................ 536/24.5
[58] Field of Search ............................... 435/6, 325, 375; 514/44; 536/23.1, 24.1, 24.31, 24.5

[56] References Cited

U.S. PATENT DOCUMENTS 5,585,479  12/1996  Hoke et al. ............................ 536/24.5

FOREIGN PATENT DOCUMENTS

88/10300  12/1988  WIPO .
92/20823  11/1992  WIPO .

OTHER PUBLICATIONS

Gura "Antisense has Growing Pains" Science 270:575–577, Oct. 27, 1995.
Madhubala et al. "Inhibition of Ornithine Decarboxylase and S–Adenosylmethionine Decarboxylase synthesis by Antisense Oligodeoxynucleotides" Mol. Cell. Biochem. 118: 191–195, 1992.
Pajunen et al. "Structure and Regulation of Mammalian S–Adenosylmethionine Decarboxylase" J. Biol. Chem. 263(32): 17040–17049, Nov. 15, 1988.
Uhlmann et al. "Antisense Oligonucleotides: A New Therapeutic Principle" Chem. Reviews 90(4):543–584, Jun. 1990.
Gewirtz et al. Facilitating oligonucleotide deliver: Helping antisense deliver on its promise. Proc. Natl. Acad. Sci. USA 93, pp. 3161–3163, Apr. 1996.
Rojanasakul. Antisense oligonucleotide therapeutics: Drug delivery and targeting. Adv. Drug Delivery Rev. 18: 115–131, 1996.
Stull et al. Antigene, ribozyme, and aptamer nucleic acid drugs: Progress and prospects. Pharm. Res. 12: 465–483, Apr. 1995.
Zon, G, "Oligonucleotide analogues as potential chemotherapeutic agents", *Pharmaceutical Research*, 5(9): 539–549 (1988).
Zon et al., "Phosphorothioate oligonucleotides", *Oligonucleotides and Analogues—A Practical Approach*, Oxford University Press, 4: 87–108 (1991).
International Search Report, PCT EP 95/02985, Jan. 19, 1996.
Agrawal, S. et al., "Pharmacokinetics, Biodistribution, and Stability of Oligodeoxynucleotide Phosphorothioates in Mice", *PNAS*, 88:7595–7599 (1991).

Crooke, R.M., et al., "In Vitro Toxicology Evaluation of ISIS 1082, A Phosphorothioate Oligonucleotide Inhibitor of Herpes Simplex Virus", *Antimicrobial Agents and Chemotherapy*, 36(3):527–532 (1992).
Madhubala, R., et al., "Inhibition of Ornithine Decarboxylase and S–adenosylmethionine Decarboxylase Synthesis by Antisense Oligodeoxynucleotides", *Molecular and Cellular Biochemistry*, 118:191–195 (1992).
Mett, H., et al., "Pharmacological Properties of the Ornithine Decarboxylase Inhibitor 3–Aminooxy–1–propanamine and Several Structural Analogues", *Cancer Chemother Pharmacol*, 32:39–45 (1993).
Meyer, T., et al., "A Derivative of Staurosporine (CGP 41 251) Shows Selectivity for Protein Kinase C Inhibition and In Vitro Anti–Proliferative as Well as In Vivo Anti–Tumor Activity", *Int. J. Cancer*, 43:851–856 (1989).
Milligan, J.F., et al., "Current Concepts in Antisense Drug Design", *Journal of Medicinal Chemistry*, 36(14):1923–1937 (1993).
Porter, C.W., et al., "Interference with Polyamine Biosynthesis and/or Function by Analogs of Polyamines or Methionine as a Potential Anticancer Chemo–Therapeutic Strategy", *Anticancer Research*, 6:525–542 (1986).
Regenass, U., et al., "New S–Adenosylmethionine Decarboxylase Inhibitors with Potent Antitumor Activity", *Cancer Research*, 52:4712–4718 (1992).
Reganass, U., et al., "CGP 48664, a New S–Adenosylmethionine Decarboxylase Inhibitor with Broad Spectrum Antiproliferative and Antitumor Activity", *Cancer Research*, 54:3210–3217 (1994).
Shantz, L.M., et al., "Purification of Human S–Adenosylmethionine Decarboxylase Expressed in *Escherichia coli* and Use of This Protein to Investigate the Mechanism of Inhibition by the Irreversible Inhibitors, 5'–Deoxy–5'–[)3–Hydrazinopropyl) Methylamino] Adenosine and 5'{[(Z)–4–Amino–2–Butenyl] Methylamino}–5'–Deoxyadenosine", *Biochemistry*, 31(29): 6848–6855 (1992).
Uhlmann, E., et al., "Antisense Oligonucleotides: A New Therapeutic Principle", *Chemical Reviews*, 90(4):543–584 (1990).

(List continued on next page.)

*Primary Examiner*—David Guzo
*Assistant Examiner*—Thomas G. Larson
*Attorney, Agent, or Firm*—Gregory D. Ferraro

[57] ABSTRACT

The invention relates to deoxyribo- and ribo-oligonucleotides and derivatives thereof, as well as pharmaceutical preparations, therapies, diagnostics and commercial research reagents in relation to disease states which respond to modulation of the synthesis of the enzyme S-adenosylmethionine decarboxylase (SAMDC). In particular, the invention relates to antisense oligonucleotides and oligonucleotide derivatives specifically hybridizable with nucleic acids relating to (preferably human) SAMDC. These oligonucleotides and their derivatives have been found to modulate the synthesis of SAMDC in cells.

2 Claims, No Drawings

OTHER PUBLICATIONS

Hill, J.R. et al., "Cell–specific Translation of S–Adenosylmethionine Decarboxylase mRNA", *The Journal of Biological Chemistry*, 267:21886–21893 (1992).

Mach, M. et al., "Isolation of a cDNA Clone Encoding S–Adenosylmethionine Decarboxylase From Bovine Lymphocytes", *Polyamines: Basice and Clinical Aspects*, 155–163 (1985).

Mach, M. et al., "Isolation of a cDNA Clone Encoding S–Adenosylmethionine Decarboxylase", *The Journal of Biological Chemistry*, 261: 11697–11703 (1986).

Pajunen, A. et al., "Structure and Regulation of Mammalian S–Adenosylmethionine Decarboxylase", *The Journal of Biological Chemistry*, 263: 17040–17049 (1988).

Suzuki, T. et al., Overproduction of S–adenosylmethionine decarboxylase in ethylglyoxal–bis(guanylhydrazone)–resistant mouse FM3A cells:, *Eur. J. Biochem.*, 215:247–253 (1993).

Waris, T. et al., "Molecular Cloning of the Mouse S–adenosylmethionine Decarboxylase cDNA: Specific Protein Binding to the Conserved Region of the mRNA 5'–Untranslated Region", *Biochemical and Biophysical Research Communications*, 189:424–429 (1992).

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
      (A) LENGTH: 20 base pairs (B) TYPE: nucleic acid
            (C) STRANDEDNESS: single
            (D) TOPOLOGY: linear (ii) MOLECULE TYPE: DNA (genomic)

(iii) ANTI-SENSE: YES (viii) POSITION IN GENOME:
            (B) MAP POSITION: -192
            (C) UNITS: bp (ix) FEATURE:
            (A) NAME/KEY: misc_feature
            (B) LOCATION: 1..20
            (D) OTHER INFORMATION: /note= "All nucleotides are of the
                phosphorothioate type"

(xi) SEQUENCE DESCRIPTION: SEQ ID NO: 1:

AATTTTCCCG GCTTTGTGTG                                                        20

(2) INFORMATION FOR SEQ ID NO: 2:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) ANTI-SENSE: YES (viii) POSITION IN GENOME:
            (B) MAP POSITION: -80
            (C) UNITS: bp (ix) FEATURE:
            (A) NAME/KEY: misc_feature
            (B) LOCATION: 1..20
            (D) OTHER INFORMATION: /note= "All nucleotides are of the
                phosphorothioate type"

(xi) SEQUENCE DESCRIPTION: SEQ ID NO: 2:

CCCGCCGCTG CCGCCGCCGC                                                        20

(2) INFORMATION FOR SEQ ID NO: 3:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) ANTI-SENSE: YES (viii) POSITION IN GENOME:
            (B) MAP POSITION: -16
            (C) UNITS: bp (ix) FEATURE:
            (A) NAME/KEY: misc_feature
            (B) LOCATION: 1..20
            (D) OTHER INFORMATION: /note= "All nucleotides are of the
                phosphorothioate type"

(xi) SEQUENCE DESCRIPTION: SEQ ID NO: 3:

CCATCACCGT GAGACTAGCG                                                        20

(2) INFORMATION FOR SEQ ID NO: 4:

(i) SEQUENCE CHARACTERISTICS:

(A) LENGTH: 20 base pairs
           (B) TYPE: nucleic acid
           (C) STRANDEDNESS: single
           (D) TOPOLOGY: linear (ii) MOLECULE TYPE: DNA (genomic)

(iii) ANTI-SENSE: YES (viii) POSITION IN GENOME:
           (B) MAP POSITION: 1
           (C) UNITS: bp (ix) FEATURE:
           (A) NAME/KEY: misc_feature
           (B) LOCATION: 1..20
           (D) OTHER INFORMATION: /note= "All nucleotides are of the
               phosphorothioate type"

(xi) SEQUENCE DESCRIPTION: SEQ ID NO: 4:

AAAAAATGTG CAGCTTCCAT                                                    20

(2) INFORMATION FOR SEQ ID NO: 5:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (genomic)

(iii) ANTI-SENSE: YES (viii) POSITION IN GENOME:
           (B) MAP POSITION: 60
           (C) UNITS: bp (ix) FEATURE:
           (A) NAME/KEY: misc_feature
           (B) LOCATION: 1..20
           (D) OTHER INFORMATION: /note= "All nucleotides are of the
               phosphorothioate type"

(xi) SEQUENCE DESCRIPTION: SEQ ID NO: 5:

GGTTTGCGTC GGGCTGCTGC                                                    20

(2) INFORMATION FOR SEQ ID NO: 6:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (genomic)

(iii) ANTI-SENSE: YES (viii) POSITION IN GENOME:
           (B) MAP POSITION: 979
           (C) UNITS: bp (ix) FEATURE:
           (A) NAME/KEY: misc_feature
           (B) LOCATION: 1..20
           (D) OTHER INFORMATION: /note= "All nucleotides are of the
               phosphorothioate type"

(xi) SEQUENCE DESCRIPTION: SEQ ID NO: 6:

TGCTGTTGTT GCTGCTTCTT                                                    20

(2) INFORMATION FOR SEQ ID NO: 7:

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) ANTI-SENSE: YES (viii) POSITION IN GENOME:
        (B) MAP POSITION: 993
        (C) UNITS: bp (ix) FEATURE:
        (A) NAME/KEY: misc_feature
        (B) LOCATION: 1..20
        (D) OTHER INFORMATION: /note= "All nucleotides are of the
            phosphorothioate type"

(xi) SEQUENCE DESCRIPTION: SEQ ID NO: 7:

TTCTTAATCA ACTCTGCTGT                                                       20

(2) INFORMATION FOR SEQ ID NO: 8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) ANTI-SENSE: YES (viii) POSITION IN GENOME:
        (B) MAP POSITION: 1046
        (C) UNITS: bp (ix) FEATURE:
        (A) NAME/KEY: misc_feature
        (B) LOCATION: 1..20
        (D) OTHER INFORMATION: /note= "All nucleotides are of the
            phosphorothioate type"

(xi) SEQUENCE DESCRIPTION: SEQ ID NO: 8:

AAAGCATCCA CCACCTTCTA                                                       20

(2) INFORMATION FOR SEQ ID NO: 9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) ANTI-SENSE: YES (viii) POSITION IN GENOME:
        (B) MAP POSITION: 1067
        (C) UNITS: bp (ix) FEATURE:
        (A) NAME/KEY: misc_feature
        (B) LOCATION: 1..20
        (D) OTHER INFORMATION: /note= "All nucleotides are of the
            phosphorothioate type"

(xi) SEQUENCE DESCRIPTION: SEQ ID NO: 9:

GCCCCCAGCA TCGACATCTA                                                       20

(2) INFORMATION FOR SEQ ID NO: 10:
```

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) ANTI-SENSE: YES (viii) POSITION IN GENOME:
            (B) MAP POSITION: 1081
            (C) UNITS: bp (ix) FEATURE:
            (A) NAME/KEY: misc_feature
            (B) LOCATION: 1..20
            (D) OTHER INFORMATION: /note= "All nucleotides are of the
                phosphorothioate type"

(xi) SEQUENCE DESCRIPTION: SEQ ID NO: 10:

TTATGGAAAG CACTGCCCCC                                                    20

(2) INFORMATION FOR SEQ ID NO: 11:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) ANTI-SENSE: YES (viii) POSITION IN GENOME:
            (B) MAP POSITION: 1108
            (C) UNITS: bp (ix) FEATURE:
            (A) NAME/KEY: misc_feature
            (B) LOCATION: 1..20
            (D) OTHER INFORMATION: /note= "All nucleotides are of the
                phosphorothioate type"

(xi) SEQUENCE DESCRIPTION: SEQ ID NO: 11:

GGGCTTTCTG CAACTACACA                                                    20

(2) INFORMATION FOR SEQ ID NO: 12:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) ANTI-SENSE: YES (viii) POSITION IN GENOME:
            (B) MAP POSITION: 1223
            (C) UNITS: bp (ix) FEATURE:
            (A) NAME/KEY: misc_feature
            (B) LOCATION: 1..20
            (D) OTHER INFORMATION: /note= "All nucleotides are of the
                phosphorothioate type"

(xi) SEQUENCE DESCRIPTION: SEQ ID NO: 12:

ACAGCAAGAG TGGCAGAGAA                                                    20

(2) INFORMATION FOR SEQ ID NO: 13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) ANTI-SENSE: YES (viii) POSITION IN GENOME:
        (B) MAP POSITION: 1361
        (C) UNITS: bp (ix) FEATURE:
        (A) NAME/KEY: misc_feature
        (B) LOCATION: 1..20
        (D) OTHER INFORMATION: /note= "All nucleotides are of the
            phosphorothioate type"

(xi) SEQUENCE DESCRIPTION: SEQ ID NO: 13:

AGAAAAGCCT TGTCTGTGGG        20

(2) INFORMATION FOR SEQ ID NO: 14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) ANTI-SENSE: YES (viii) POSITION IN GENOME:
        (B) MAP POSITION: 1394
        (C) UNITS: bp (ix) FEATURE:
        (A) NAME/KEY: misc_feature
        (B) LOCATION: 1..20
        (D) OTHER INFORMATION: /note= "All nucleotides are of the
            phosphorothioate type"

(xi) SEQUENCE DESCRIPTION: SEQ ID NO: 14:

AGAGGGTTAG GCTGAGGCCA        20

(2) INFORMATION FOR SEQ ID NO: 15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) ANTI-SENSE: YES (viii) POSITION IN GENOME:
        (B) MAP POSITION: 1483
        (C) UNITS: bp (ix) FEATURE:
        (A) NAME/KEY: misc_feature
        (B) LOCATION: 1..20
        (D) OTHER INFORMATION: /note= "All nucleotides are of the
            phosphorothioate type"

(xi) SEQUENCE DESCRIPTION: SEQ ID NO: 15:

GGATGTAAAA TTCTGGCAGC        20

```
(2) INFORMATION FOR SEQ ID NO: 16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) ANTI-SENSE: YES (vi) ORIGINAL SOURCE:
        (A) ORGANISM: Herpes Simplex Virus (ix) FEATURE:
        (A) NAME/KEY: misc_feature
        (B) LOCATION: 1..21
        (D) OTHER INFORMATION: /note= "All nucleotides are of the
            phosphorothioate type"

(xi) SEQUENCE DESCRIPTION: SEQ ID NO: 16:

GCCGAGGTCC ATGTCGTACG C                                              21
```

ANTITUMOR ANTISENSE OLIGONUCLEOTIDES

This is a Continuation of Ser. No. 08/287,753, filed Aug. 9, 1994, now abandoned.

This invention relates to deoxyribo- and ribo-oligonucleotides and derivatives thereof, as well as pharmaceutical preparations, therapies, diagnostics and commercial research reagents in relation to disease states which respond to modulation of the synthesis of the enzyme S-adenosylmethionine decarboxylase (SAMDC). In particular, the invention relates to antisense oligonucleotides and oligonucleotide derivatives specifically hybridizable with nucleic acids relating to (preferably human) SAMDC. These oligonucleotides and their derivatives have been found to modulate the synthesis of SAMDC in cells.

SAMDC is a key enzyme in polyamine biosynthesis. Specific inhibitors showing direct inhibition of the enzyme cause cessation of cell proliferation accompanied by depletion of cellular polyamine pools and show tumoristatic activity in animals; (see Regenass et al., Cancer Res. 54, 3210–7 (1994)). These inhibitors are therefore appropriate for the treatment of diseases that respond to depletion of cellular polyamine pools, for example proliferative diseases, such as tumors. However, a complete understanding of enzyme mechanism is needed to design specific inhibitors.

SAMDC is an enzyme with very high turnover rate, thus showing a very short half-life in vivo (about 50 min or even less; see Pegg, J. Biol. Chem. 254, 3249–53 (1979)). Decreased biosynthesis of this protein might therefore lead to a decrease in enzyme activity and thus result in a depletion of cellular spermidine and spermine pools, firnally resulting in cytostasis and potentially apoptotic cell death.

Surprisingly, it has been found that the compounds mentioned below show the capability to modulate SAMDC synthesis in cells. They are therefore appropriate for the prevention and therapeutic treatment of diseases that respond to this modulation, especially inhibition, of SAMDC synthesis and thus of enzyme activity, such an inhibition having as one effect a modulation of polyamine biosynthesis, such as a lowering of the spermine and spermidine pools in cells. Especially, the compounds of the invention have a good antiproliferative activity.

The instant invention circumvents problems encountered by prior workers by modulating the biosynthesis of SAMDC, rather than inhibiting the enzyme directly, to achieve the therapeutic effect.

In accordance with the present invention, oligonucleotides and their derivatives (as well as salts thereof where salt-forming groups are present) are provided that are specifically hybridizable with DNA or RNA, preferably mRNA, deriving from the gene that encodes functional SAMDC, preferably human SAMDC. Such an oligonueleotide or oligonucleotide derivative comprises nucleotide units or analogues/derivatives thereof sufficient in number and identity to allow such hybridization. This relationship is commonly denominated as "antisense", and the compounds of the invention are thus antisense oligonucleotides or their derivatives.

Antisense oligonucleotides and their derivatives specifically bind (hybridize) to the complementary sequence of DNA, pre-mRNA or mature mRNA, as defined by Watson-Crick base pairing, interfering with the flow of genetic information frorr DNA to SAMDC protein.

In one preferred embodiment of the invention, the oligonucleotides or their derivatives are specifically hybridizable with the 3' untranslated region of the mRNA coding for SAMDC (especially human SAMDC), more preferably having a sequence corresponding to that of human SAMDC cDNA as described in the literature (see Pajunen et al., J. Biol. Chem. 263(32), 17040–9 (1988)) and allelic variants thereof. More preferred due to their unexpectedly high effectivity in the test systems described below are oligonucleotides and derivatives thereof corresponding to a part of the sequence ranging from base position 1060 (5') to 1557 (3') of human cDNA for SAMDC (preferably of the sequence described by Pajunen et al, see above), oligonucleotide derivatives corresponding to a part of the sequence ranging from base position 1065 to 1105 being most preferred (base positions are given with respect to the first (5') nucleotide of the start codon of the mRNA corresponding to said cDNA). Of these compounds, oligonucleotide derivatives corresponding to (preferably of) the sequences described below by SEQ ID NO: 10 and especially by SEQ ID NO: 9 are by far most preferred.

In another preferred embodiment of the invention, the oligonucleotides or oligonucleotide derivatives are specifically hybridizable to the 5' noncoding region of SAMDC mRNA, and preferably their sequence is corresponding to a part of the sequence ranging from base position –248 (5') to –20 (3') of human SAMDC cDNA, more preerably to the region corresponding to a part of the sequence ranging from base position –85 to –55. Of these compounds, oligonucleotide derivatives of the sequence described below by SEQ ID NO: 2 are most preferred.

Generally, oligonucleotide derivatives are preferred over oligonucleotides as such.

Within the present specification, the general terms and definitions used hereinbefore and hereafter preferably have the following meanings:

The present compounds can be isomerically pure or they can be present in isomeric mixtures. Thus, if asymmetric phosphorus atoms are present, the compounds can be present as diastereomeric mixtures or as pure diastereomeres.

Some of the oligonucleotides or oligonucleotide derivatives can be present in different tautomeric forms, depending inter alia on the solvent and the ionization status of ionizable groups. Thus, for example, the central group in phosphorothioate; [O—(P—SH)(=O)—O] being tautomerizable to [O—(P=S)(—OH)—O] with the more stable form depending, among others, on the solvent and the state of ionization. Within the present specification, the term oligonucleotide derivatives is also to be understood to encompass these tautomeric forms, the presence of which is know to the person skilled in the art.

The prefix "lower" denotes a radical with up to and including 7 carbon atoms, preferably up to and including 4, and most preferably with up to and including 2 carbon atoms.

The term "modulation of the synthesis SAMDC" preferably means an inhibition of the biosynthesis of SAMDC which leads to diminished concentration of the active enzyme in cells.

The term "corresponding" means that the given compound has base pairing characteristics comparable to the nucleic acid sequence referred to, that is, comparable hybridization characteristics.

Antisense oligonucleotides or oligonucleotide derivatives according to the invention comprising nucleotide units or analogues/derivatives thereof sufficient in number and identity to allow hybridization preferably have a length that allows specific binding to the target sequence, especially a length corresponding to 5 to 50 nucleotide units, preferably to 10 to 35 nucleotide units, more preferably to 15 to 22 nucleotide units, and most preferably to 18 to 20 nucleotide units.

In order to allow also for the inclusion of allelic variants of the human SAMDC gene and for hybridizable oligonucleotides or oligonucleotide analogues that show minor numbers of mispairing that still allow hybridization, the sequences can vary from those corresponding to the human cDNA (preferably as decribed by Pajunen et al., see above) by some nucleotides or nucleotide analogues; preferably, up to 3 nucleotides or nucleotide analogues can differ in the sequence of a given oligonucleotide or oligonucleotide derivative with respect to the corresponding SAMDC cDNA, monr preferably in the sense of conservative mutations.

A nucleotide unit is a base-sugar or base-sugar analogue combination suitably bound to an adjacent nucleotide unit through phosphodiester or other bonds.

The oligonucleotides or oligonucleotide derivatives according to the invention can be designed to selectively inhibit a given isozyme or particular set of isozymes, or to inhibit all members of a given family of isozymes of SAMDC.

In the context of this invention, the term "oligonucleotide" refers to an oligonucleotide formed from naturally occurring base radicals and pentofuranosyl (ribosyl or (preferably) 2'-deoxyribosyl) groups or modified forms thereof joined by native phosphodiester bonds, that is which comprises building blocks of the following formulae I and/or I* wherein Q is H or OH:

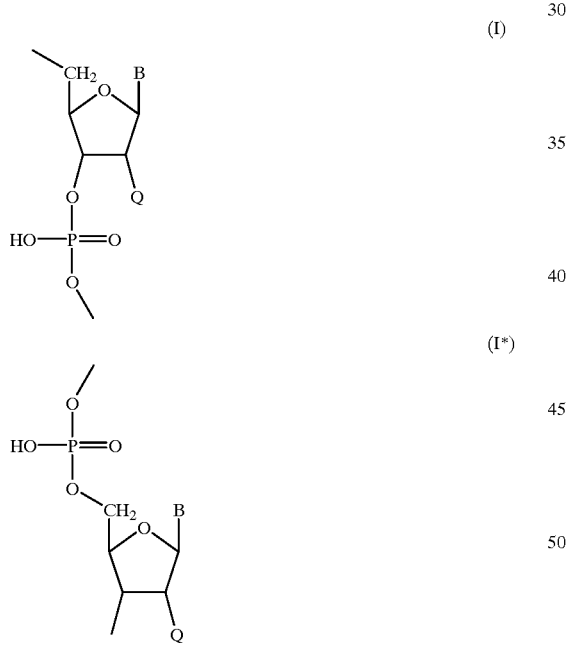

wherein B is a radical of a base selected from adenine, cytosine, 5-methylcytosine, thymine and guanine.

The term "oligonucleotide derivative" also refers to synthetic species derived from naturally occurring nucleotide subunits or their close homologs and may also refer to moieties which function similarly to naturally occurring oligonucleotides but which have non-naturally occurring portions, for example at least one building block that differs from the building blocks of a natural oligonucleotide. Thus, oligonucleotides with regard to their backbone may have altered sugar moieties and/or inter-sugar linkages, and, with regard to the bases, altered bases may be present.

Such oligonucleotide derivatives are best described as being functionally interchangeable with natural oligonucleotides (or synthesized oligonucleotides along natural lines), but having one or more differences from natural structure. All such oligonucleotides are comprehended by this invention so long as they function effectively to show the hybridization properties to DNA or RNA deriving from the SAMDC gene, preferably to mRNA.

With regard to the backbone, that is to the altered sugar moieties and/or inter-sugar linkages, preferred among these are the following types:

Species derived from naturally occurring nucleotide subunits or their close homologs of formula I or I* wherein B is a base radical as defined below and Q is SH, SCH3, F, $N_3$, CN, OCN, $O(CH_2)_zNH_2$ or $O(CH_2)_zCH_3$ where z is from 1 to about 10 or $O(CH_2CH_2O)_vCH_3$ wherein v is from 0 to 12, preferably v is 0 or 1; or Q is also in a broader sense another substituent having similar properties, for example selected from Cl, Br, $CF_3$, $ONO_2$, $NO_2$, $NH_2$ and O—, S— or NH-lower alkyl; phosphorothioate and in a broader sense other species such as phosphorodithioate, sulfate, sulfonate, sulfonamide, sulfone, sulfite, sulfoxide, sulfide, formacetal, 3'-thioformacetal, 5'-thioether, hydroxylamine (with $CH_2$—NH—O—$CH_2$ instead of the phosphodiester bond O—[(HO—)P(=O)]—O—$CH_2$), methylene(methylimino) (with $CH_2$—N($CH_3$)—O—$CH_3$ instead of the phosphodiester bond); methyleneoxy(methylimino) (with $CH_2$O—N($CH_3$)—$CH_2$ instead of the phosphodiester bond), methylene-((methylimino)-methylimino) (with $CH_2$—N($CH_3$)—N($CH_3$)—$CH_2$ instead of the phosphodiester bond), carbonate, 5'-N-carbamate, amide (with $CH_2$—(C=O)—NH—$CH_2$ instead of the phosphodiester bond, see International Application WO 92/20823) morpholino-carbamate (see Summerton, J. E. and Weller, D. D., U.S. Pat. No: 5,034,506) or peptide nucleic acid (see P. E. Nielsen, M. Egholm, R. H. Berg, O. Buchardt, Science 254, 1497 (1991)) which are known for use in the art (for reviews with references concerning these modified nucleotides, see Milligan et al., J. Med. Chem. 36(14), 1923–37 (1993), and Uhlmann et al., Chemical Reviews 90(4), 543–84 (1990)). In accordance with some preferred embodiments, at least one of the phosphodiester bonds of the oligonucleotide has been substituted with a structure which functions to enhance the ability of the compositions to penetrate into the region of cells where the RNA or DNA whose activity to be modulated is located and in order to avoid extensive degradation of the oligonucleotide derivative due to nucleases that would result in ineffective cleavage products. It is preferred that such substitutions comprise phosphorothioate bonds, phosphorodithioate bonds, methyl phosphonate bonds, phosphoramidate bonds, boranophosphate bonds, phosphotriester bonds, short chain alkyl or cycloalkyl structures, or heteroatom-substituted short chain alkyl structures, and most especially phosphorothioate bonds.

Preferred of these are oligonucleotide derivatives which (in their nucleotide/nucleotide derivative sequence) comprise at least one of the following units (bivalent radicals) of the formulae given hereinafter, wherein B is a base radical as defined below; Q is SH, SCH3, F, $N_3$, CN, OCN, $O(CH_2)_zNH_2$ or $O(CH_2)_zCH_3$ where z is from 1 to about 10 or $O(CH_2CH_2O)_vCH_3$ wherein v is from 0 to 12, or in a broader sense another substituent having similar properties, for example selected from Cl, Br, $CF_3$, $ONO_2$, $NO_2$, $NH_2$ and O—, S— or NH-lower alkyl, most especially Q being hydroxy or preferably hydrogen; and the other moieties have the meanings given behind the respective formula:

(IIa–IIf)

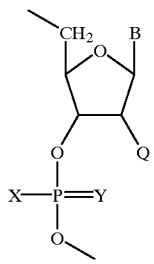

(IIa*–IIf*)

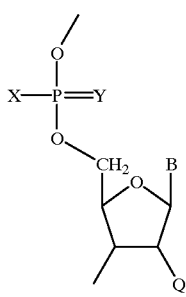

| Radical of formula | type | | |
|---|---|---|---|
| (IIa), (IIa*) | phosphorothioate | X = SH | Y = O |
| (IIb), (IIb*) | phosphorodithioate | X = SH | Y = S |
| (IIc), (IIc*) | methylphosphonate | X = $CH_3$ | Y = O |
| (IId), (IId*) | phosphoramidate | X = NH—R | Y = O |
| (IIe), (IIe*) | boranophosphate | X = $BH_3$ | Y = O |
| (IIf), (IIf*) | phosphotriester | X = O—R | Y = O | wherein R is lower alkyl;

(IIIa–IIIh)

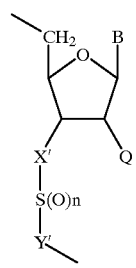

(IIIa*–IIIh*)

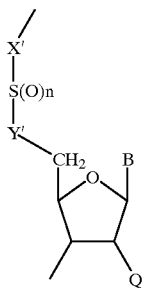

| Radical of formula | type | n | X' | Y' |
|---|---|---|---|---|
| (IIIa), (IIIa*) | sulfate | 2 | O | S |
| (IIIb), (IIIb*) | sulfonate | 2 | O | $CH_2$ |
| (IIIc), (IIIc*) | sulfamate | 2 | O | NH |
| (IIId), (IIId*) | sulfonamide | 2 | NH | $CH_2$ |
| (IIIe), (IIIe*) | sulfone | 2 | $CH_2$ | $CH_2$ |
| (IIIf), (IIIf*) | sufite | 1 | O | O |
| (IIIg), (IIIg*) | sulfoxide | 1 | $CH_2$ | $CH_2$ |
| (IIIh), (IIIh*) | sulfide | 0 | $CH_2$ | $CH_2$ |

(IVa–IVd)

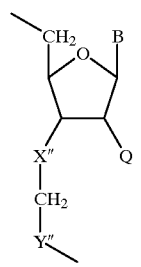

(IVa*–IVd*)

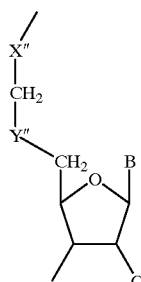

| Radical of formula | type | X" | Y" |
|---|---|---|---|
| (IVa), (IVa*) | formacetal | O | O |
| (IVb), (IVb*) | 3'-thioformacetal | S | O |
| (IVc), (IVc*) | 5'-thioformacetal | O | S |
| (IVd), (IVd*) | thioether | $CH_2$ | S |

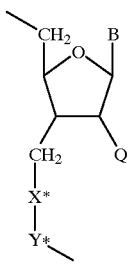 (Va–Vc)

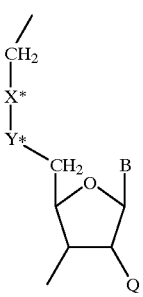 (Va*–Vc*)

| Radical of formula | type | X* | Y* |
|---|---|---|---|
| (Va), (Va*) | hydroxylamine | N—H | O |
| (Vb), (Vb*) | methylene(methyl-imino) | N—CH₃ | O |
| (Vc), (Vc*) | methyleneoxy(methyl-imino) | O | N—CH₃ |

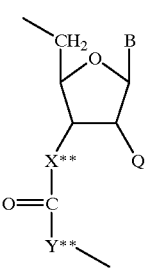 (VIa–VId)

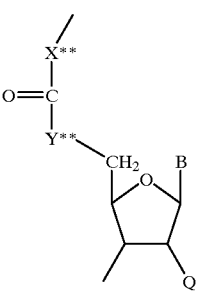 (VIa*–VId*)

| Radical of formula | type | X | Y |
|---|---|---|---|
| (VIa), (VIa*) | carbonate | O | O |
| (VIb), (VIb*) | 5'-N-carbamate | O | NH |
| (VIc), (VIc*) | amide | CH₂ | NH |
| (VId), (VId*) | amide II | NH | CH₂ |

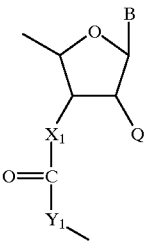 (VII)

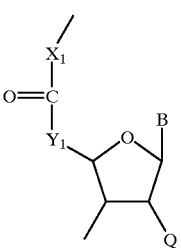 (VII*)

| Radical of formula | type | X₁ | Y₁ |
|---|---|---|---|
| (VII), (VII*) | amide III | NH | CH₂ |

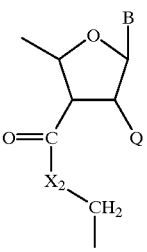 (VIII)

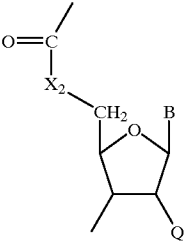 (VIII*)

| Radical of formula | type | X₂ |
|---|---|---|
| (VIII), (VIII*) | amide IV | NH |

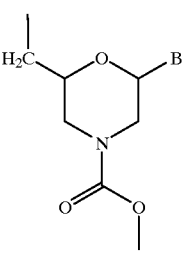 (IX)

-continued

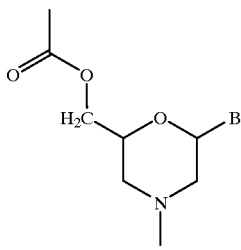

(IX*)

| Radical of formula | type |
|---|---|
| IX, IX* | morpholino-carbamate |

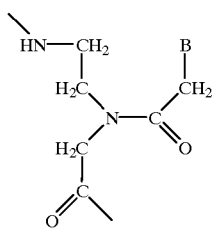

(X)

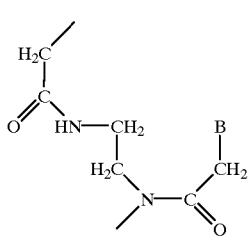

(X*)

| Radical of formula | type |
|---|---|
| X, X* | peptide nucleic acid |

The oligonucleotide derivatives can be composed of a combination of these units, or they can preferably comprise only one type of these units with regard to the backbone (sugar moieties and/or inter-sugar linkages) which is present throughout the chain of the respective oligonucleotide derivative, most preferably of the 2'-deoxyribose-phosphorothioate type. At the 5'- and 3'-termini of the respective oligonucleotide derivative molecules, the free valency of the radicals of any of the above formulae I, I*, II to X and II* to X* is bonded preferably to hydrogen if the terminal atom is selected from N, O and S and to hydroxy or an analogue thereof, such as halogen, for exarmple Cl, Br or I, Mercapto (SH) or Azido ($N_3$), if the terminal atom is C, more preferably to one of the following residues, but may also (in a broader aspect of the invention) be bound to other conjugated moieties as described below forming conjugates:

In compounds with a terminal moiety of any one of the formulae I, IIa–IIf, IIIa, IIIc, IIIf, IVa–IVd, Va–Vc, VIa–VIc, IX and X*, the 5' terminus is preferably bonded to a terminal OH group, and the 3'-terminus to a hydrogen.

In compounds with a terminal moiety of any one of the formulae IX*, IIa*–IIf*, IIIa*–IIIh*, IVa*–IVc*, Va*–Vc*, VIa*–VId*, VII*, VIII* and X, the 5'-terminus is preferably bonded to a terminal hydrogen, and the 3'-terminus to a OH group.

In compounds with a terminal moiety of any one of the formulae IX*, the 5'-terminus is preferably bonded to a terminal OH group which is bonded replacing the terminal —(C═O)—O, and the 3'-terminus to a hydrogen atom.

In compounds with a terminal moiety of any one of the formulae IIIb, IIId, IIIe, IIIe*, IIIg, IIIg*, IIIh, IIIh*, IVd*, VId, VII, VIII and VIII*, the 5'-terrninus is preferably bonded to a terminal OH group and the 3'-terminus is preferably bonded to an OH group.

In order to allow for modified and improved pharmacokinetic properties, such as enhanced uptake into cells or the oligonucleotides or oligonucleotide derivatives according to the invention can also be conjugated to one or more (then identical or different) additional moieties, for example selected from: A group forming micelles, an antibody, a carbohydrate, a receptor-binding group, a steroid, such as cholesterol, a polypeptide, an intercalating agent, such as an acridine derivative, a long-chain alkohol, a phospholipid and other lipophilic groups.

The very most preferred of the oligonucleotide derivatives are those of the phosphorothioate type.

B in any of the formulae (Ii) to (Xi) and (Ii*) to (Xi*) ("i" standing for the respective indices in the formulae above, such as, for example, "a", "b" or n) index if none is required) is a base radical and is selected from the group comprising a purine radical or an analogue thereof and a pyrimidine radical or an analogue thereof.

If B is a purine radical or an analogue thereof, it may be a radical of formula XI, XIa, XIb, XIc, XId, XIe or XIf

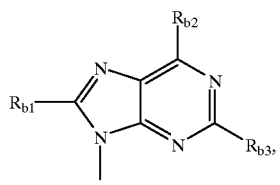

(XI)

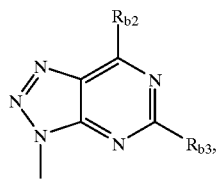

(XIa)

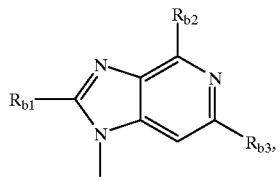

(XIb)

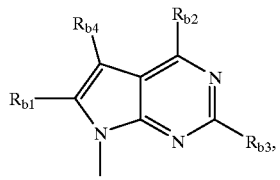

(XIc)

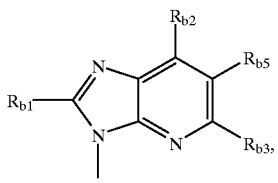
(XId)

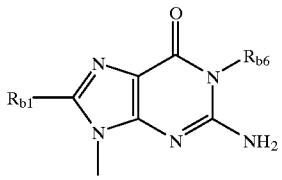
(XIe)

or

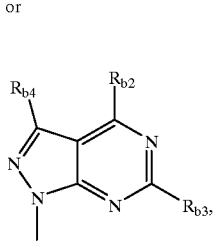
(XIf)

wherein $R_{b1}$ is H, Cl, Br, OH or —O—$C_1$–$C_{12}$alkyl, and $R_{b2}$, $R_{b3}$ and $R_{b5}$ are each independently of the others H, OH, SH, $NH_2$, $NHNH_2$, NHOH, NHO-$C_{1-12}$alkyl, —N=CH—N($C_1$–$C_{12}$alkyl)$_2$, F, Cl, Br, $C_1$–$C_{12}$alkyl, hydroxy-$C_1$–$C_{12}$alkyl, amino-$C_1$–$C_{12}$alkyl, $C_1$–$C_{12}$alkoxy, benzyloxy or $C_1$–$C_{12}$alkylthio, the hydroxy and amino groups being present as such or substituted by a protecting group; or phenyl, benzyl, primary amino having from 1 to 20 carbon atoms or secondary amino having from 2 to 30 carbon atoms, $R_{b4}$ is hydrogen, CN or —C≡C-$R_{b7}$, and $R_{b6}$ and $R_{b7}$ are hydrogen or $C_1$–$C_4$alkyl.

Protecting groups and processes for derivatising hydroxy groups Leaving such protecting groups are generally known in sugar and nucleotide chemistry and are described in standard text books (see, for example, Greene, B. T., Protective Groups in Organic Synthesis, Wiley Interscience, New York (1991), Sonveaux, E., Bioorganic Chemistry 14:274–325 (1986) or Beaucage, S. L., Iyer, R., Tetrahedron 48:22.23–2311 (1992)). Examples of such protecting groups are: benzyl, methylbenzyl, dirnethylbenzyl, methoxybenzyl, dimethoxybenzyl, bromobenzyl, 2,4-dichlorobenzyl; diphenylmethyl, di(methylphenyl)methyl, di(dimethylphenyl)methyl, di(methoxyphenyl)methyl, di(dimethoxyphenyl)methyl, triphenylmethyl, tris-4,4',4"-tert-butylphenylmethyl, di-p-anisylphenylmethyl, tri(methylphenyl)methyl, tri(dimethylphenyl)methyl, metlioxyphenyl(diphenyl)methyl, di(methoxyphenyl)phenylmethyl, tri(methoxyphenyl)metliyl, tri(dimethoxyphenyl)methyl; triphenylsilyl, alkyldiphenylsilyl, dialkylphenylsilyl and trialkylsilyl having from 1 to 20, preferably from 1 to 12, and especially from 1 to 8, carbon atoms in the alkyl groups, for example trimethylsilyl, triethylsilyl, tri-n-propylsilyl, isopropyl-dimethylsilyl, tert-butyl-dimethylsilyl, tert-butyl-diphenylsilyl, n-octyl-dimethylsilyl, (1,1,2,2-tetramethylethyl)-dimethylsilyl; -($C_1$–$C_8$alkyl)$_2$Si—O—Si($C_1$–$C_8$alkyl)$_2$—, wherein alkyl is, for example, methyl, ethyl, n- and iso-propyl or n-, iso- or tert-butyl; $C_2$–$C_{12}$acyl, especially $C_2$–$C_8$acyl, such as acetyl, propanoyl, butanoyl, pentanoyl, hexanoyl, benzoyl, methylbenzoyl, methoxybenzoyl, chlorobenzoyl and bromobenzoyl; $R_{S1}$—$SO_2$— wherein $R_{S1}$ is $C_1$–$C_{12}$alkyl, especially $C_1$–$C_6$alkyl, $C_5$- or $C_6$-cycloalkyl, phenyl, benzyl, $C_1$–$C_{12}$alkylphenyl, especially $C_1$–$C_4$alkylphenyl, or $C_1$–$C_{12}$alkylbenzyl, especially $C_1$–$C_4$alkylbenzyl, or halophenyl or halobenzyl, for example methyl-, ethyl-, propyl-, butyl-, phenyl-, benzyl-, p-bromo-, p-methoxy- and p-methylphenyl-sulfonyl; $C_1$–$C_{12}$alkoxycarbonyl, preferably $C_1$–$C_8$alkoxycarbonyl, that is unsubstituted or substituted by F, Cl, Br, $C_1$–$C_4$alkoxy, tri($C_1$–$C_4$alkyl)silyl or by $C_1$–$C_4$alkylsulfonyl, for example methoxy-, ethoxy-, n- or iso-propoxy- or n-, iso- or tert-butoxycarbonyl, 2-trimethylsilylethoxycarbonyl, 2-methylsulfonylethoxycarbonyl, allyloxycarbonyl, or phenoxycarbonyl or benzyloxycarbonyl that is unsubstituted or is substituted as for alkoxycarbonyl, for example methyl- or methoxy- or chloro-phenoxycarbonyl or methyl- or methoxy- or chloro-benzyloxycarbonyl, and 9-fluorenylmethoxycarbonyl. If a hydroxy protecting group is alkyl, this moiety may be substituted by fluorine, chlorine, bromine, $C_1$–$C_4$alkoxy, phenoxy, chlorophenoxy, methoxyphenoxy, benzyloxy, methoxybenzyloxy or by chlorophenoxy. If more than one hydroxy group is protected in the respective oligonucleotide or its derivative, the protecting groups may be identical or different.

Protecting groups and processes for derivatising amino groups (as well as imino groups, "amino" groups in the following paragraphs that refer to amino protecting groups also, if possible, meaning imino) having such protecting groups are generally known in sugar, amino acid and nucleotide chemistry and are described, for example, in standard text books (see J. F. W. McOmie, "Protective Groups in Organic Chemistry", Plenum Press, London and New York 1973; Th. W. Greene, "Protective Groups in Organic Synthesis", Wiley, New York 1981, in "The Peptides", Volume 3 (E. Gross and J. Meienhofer, eds.), Academic Press, London and New York 1981; "Methoden der orginischen Chemie", Houben-Weyl, 4th edition, Volume 15/I, Georg Thieme Verlag, Stuttgart 1974; and H.-D. Jakubke and H. Jescheit, "Aminosäuren, Peptide, Proteine" ("Amino acids, peptides, proteins"), Verlag Chemie, Weinheim, Deerfield Beach and Basle 1982).

A protected amino group may be protected, for example, in the form of an acylamino, arylmethylamino, etherified mercaptoamino, 2-acyl-lower alk-1-enylamino, silylamino or N-lower alkylpyrrolidinylidene group or in the form of an azido group.

In a corresponding acylamino group, acyl is, for example, the acyl radical of an organic carboxylic acid having, for example, up to 18 carbon atoms, especially an unsubstituted or substituted, for example halo- or aryl-substituted, lower alkanecarboxylic acid or an unsubstituted or substituted, for example halo-, lower alkoxy- or nitro-substituted, benzoic acid, or, preferably, of a carbonic acid semiester. Such acyl groups are, for example, lower alkanoyl, such as formyl, acetyl, propionyl, isobutyryl or pivaloyl, halo-lower alkanoyl, for example 2-haloacetyl, such as 2-chloro-, 2-bromo-, 2-iodo-, 2,2,2-trifluoro- or 2,2,2-trichloro-acetyl, phenyoxy- or (lower alkoxy)phenoxy-lower alkyl, such as phenoxyacetyl or 4-tert-butylphenoxyacetyl, unsubstituted or substituted, for example halo-, lower alkoxy-, or nitro-substituted, benzoyl, such as benzoyl, 4-chlorobenzoyl, 4-methoxybenzoyl or 4-nitrobenzoyl, lower alkoxycarbonyl, preferably lower alkoxycarbonyl that is branched in the 1-position of the lower alkyl radical or suitably substituted in the 1- or 2-position, for example tert-lower alkoxycarbonyl, such as tert-but-oxycarbonyl, arylmethoxycarbonyl having one, two or three aryl radicals which are phenyl that is unsubstituted or mono- or poly-substituted, for example, by lower alkyl, especially tert-lower alkyl, such as tert-butyl, lower alkoxy, such as methoxy, hydroxy, halogen, such as chlorine, and/or by nitro, for example benzyloxycarbonyl, 4-nitrobenzyloxycarbonyl, diphenylmethoxycarbonyl, 9-fluorenylmethoxycarbonyl or di(4-methoxyphenyl) methoxycarbonyl, aroylmethoxycarbonyl wherein the aroyl group is preferably benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, 2-(tri-substituted silyl)-lower alkoxycarbonyl, for example 2-tri-lower alkylsilyl-lower alkoxycarbonyl, such as 2-trimethylsilylethoxycarbonyl or 2-(di-n-butyl-methyl-silyl)-ethoxycarbonyl, triarylsilyl-lower alkoxycarbonyl, for example 2-triphenylsilylethoxycarbonyl, or N,N-di-lower alkylformamidinyl, such as N,N-dimethylformamidinyl.

In an arylmethylamino group, for example a mono-, di- or especially tri-arylmethylamino group, the aryl radicals are especially unsubstituted or substituted phenyl radicals. Such groups are, for example, benzyl-, diphenylmethyl- or especially trityl-amino.

In an etherified mercaptoamino group the mercapto group is especially in the form of substituted arylthio or aryl-lower alkylthio, wherein aryl is, for exaLmple, phenyl that is unsubstituted or substituted, for example, by lower alkyl, such as methyl or tert-butyl, lower alkoxy, such as methoxy, halogen, such as chlorine, and/or by nitro, for example 4-nitrophenylthio.

In a 2-acyl-lower alk-1-enyl radical that can be used as an amino-protecting group, acyl is, for example, the corresponding radical of a lower alkanecarboxylic acid, of a benzoic acid that is unsubstituted or substituted, for example, by lower alkyl, such as methyl or tert-butyl, lower alkoxy, such as methoxy, halogen, such as chlorine, and/or by nitro, or especially of a carbonic acid semiester, such as a carbonic acid lower alkyl semiester. Corresponding protecting groups are especially 1-lower alkanoyl-lower alk-1-en-2-yl, for example 1-lower alkanoylprop-1-en-2-yl, such as 1-acetylprop-1-en-2-yl, or lower alkoxycarbonyl-lower alk-1-en-2-yl, for example lower alkoxycarbonylprop-1-en-2-yl, such as 1-ethoxycarbonylprop-1-en-2-yl.

A silylamino group is, for example, a tri-lower alkylsilylamino group, for example trimethylsilylamino or tert-butyl-dimethylsilylamino. The silicon atom of the silylamino group can also be substituted by only two lower alkyl groups, for example methyl groups, and by the amino group or carboxy group of a second molecule of a compound according to the invention. Compounds having such protecting groups can be prepared, for example, using the corresponding chlorosilanes, such as dimethylchlorosilane, as silylating agents.

An N-lower alkylpyrrolidinylidene group is preferably N-methylpyrrolidin-2-ylidene.

Preferred amino-protecting groups are lower alkoxycarbonyl, phenyl-lower alkoxycarbonyl, fluorenyl-lower alkoxycarbonyl, 2-lower alkanoyl-lower alk-1-en-2-yl and lower alkoxycarbonyl-lower alk-1-en-2-yl, with most preference being given to isobutyryl, benzoyl, phenoxyacetyl, 4-tert-butylphenoxyacetyl, N,N-dimethylformamidinyl and/or N-methylpyrrolidin-2-ylidene.

Primary amino (for example in the definition of $R_{b2}$, $R_{b3}$ and $R_{b5}$) contains preferably from 1 to 12, and especially from 1 to 6, carbon atoms, and secondary amino (for example in the definition of $R_{b2}$, $R_{b3}$ and $R_{b5}$) contains preferably from 2 to 12, and especially from 2 to 6, carbon atoms.

Some examples of alkyl, alkoxy, alkylthio, hydroxyalkyl and aminoalkyl containing preferably from 1 to 6 carbon atoms are methyl, ethyl and the isomers of propyl, butyl, pentyl, hexyl, heptyl, octyl, nonyl, decyl, undecyl and dodecyl, ancl corresponding alkoxy, alkylthio, hydroxyalkyl and aminoalkyl radicals. Alkyl, alkoxy, all ylthio, hydroxy-alkyl and aminoalkyl contain especially from 1 to 4 carbon atoms. Preferred alkyl, alkoxy, alkylthio, hydroxyalkyl and aminoalkyl radicals are methyl, ethyl, n- and iso-propyl, n-, iso- and tert-butyl, methoxy, ethoxy, methylthio and ethylthio, aminomethyl, aminoethyl, hydroxymethyl and hydroxyethyl.

The primary amino and the secondary amino may be, for example, radicals of the formula $R_{a1}R_{a2}N$, wherein $R_{a1}$ is hydrogen or, independently, has the definition of $R_{a2}$, and $R_{a2}$ is $C_1$–$C_{20}$-, preferably $C_1$–$C_{12}$- and especially $C_1$–$C_6$-alkyl, $C_1$–$C_{20}$-, preferably $C_1$–$C_{12}$- and especially $C_1$–$C_6$-aminoalkyl, $C_1$–$C_{20}$-, preferably $C_1$–$C_{12}$- and especially $C_1$–$C_6$-hydroxyalkyl; carboxyalkyl or carbalkoxyalkyl, the carbalkoxy group containing from 2 to 8 carbon atoms and the alkyl group from 1 to 6, preferably from 1 to 4, carbon atoms; $C_2$–$C_{20}$-, preferably $C_2$–$C_{12}$- and especially $C_2$–$C_6$-alkenyl; phenyl, mono- or di-($C_1$–$C_4$-alkyl or $C_1$–$C_4$alkoxy) phenyl, benzyl, mono- or di-($C_1$–$C_4$alkyl or $C_1$–$C_4$alkoxy) benzyl; or 1,2-, 1,3- or 1,4-imidazolyl-$C_1$–$C_6$alkyl, or $R_{a1}$ and $R_{a2}$ together are tetra- or penta-methylene, 3-oxa-1,5-pentylene, —CH$_2$—NR$_{a3}$—CH$_2$CH$_2$— or —CH$_2$CH$_2$—NR$_{a3}$—CH$_2$CH$_2$—, wherein $R_{a3}$ is hydrogen or $C_1$–$C_4$alkyl. The amino group in aminoalkyl may be substituted by one or two $C_1$–$C_4$alkyl or $C_1$–$C_4$hydroxyalkyl groups. The hydroxy group in hydroxyalkyl may be etherified by $C_1$–$C_4$alkyl.

Examples of alkyl are given hereinbefore. Examples of aminoalkyl are aminomethyl, aminoethyl, 1-aminoprop-2-yl or -3-yl, 1-amino-but-2-yl or -3-yl or -4-yl, N-methyl- or N,N-dimethyl- or N-ethyl- or N,N-diethyl- or N-2-hydroxyethyl- or N,N-di-2-hydroxyethyl-aminomethyl or -aminoethyl or -aminopropyl or -aminobutyl. Examples of hydroxyalkyl are hydroxymethyl, 1-hydroxy-eth-2-yl, 1-hydroxy-prop-2- or -3-yl and 1-hydroxybut-2-yl, -3-yl or -4-yl. Examples of carboxyalkyl are carboxymethyl, carboxyethyl, carboxypropyl and carboxybutyl, and examples of carbalkoxyalkyl are those carboxyalkyl groups esterifed by methyl or by ethyl. Examples of alkenyl are allyl, but-1-en-3-yl or -4-yl, pent-3- or -4-en-1-yl or -2-yl, hex-3- or -4- or -5-en-1-yl or -2-yl. Examples of alkyl- and alkoxy-phenyl and alkyl- and alkoxy-benzyl are methylphenyl, dimethylphenyl, ethylphenyl, diethylphenyl, methylbenzyl, dimethylbenzyl, ethylbenzyl, diethylbenzyl, methoxyphenyl, dimethoxyphenyl, ethoxyphenyl, diethoxyphenyl, methoxybenzyl, dimethoxybenzyl, ethoxybenzyl and diethoxybenzyl. Examples of imidazolylalkyl in which the alkyl group preferably contains from 2 to 4 carbon atoms are 1,2-, 1,3- or 1,4-imidazolyl-ethyl or -n-propyl or -n-butyl. $R_{a3}$ is preferably hydrogen, methyl or ethyl.

Preferred examples of primary amino and secondary amino are methyl-, ethyl-, dimethyl-, diethyl-, allyl-, mono- or di-(1-hydroxy-eth-2-yl)-, phenyl- and benzyl-amino, acetylamino, isobutyrylamino and/or benzoylamino.

In a preferred form, $R_{b1}$ is hydrogen. In another preferred form, $R_{b5}$ is hydrogen. In a further preferred form, $R_{b2}$ and $R_{b3}$ are each independently of the other H, F, Cl, Br, OH, SH, $NH_2$, NHOH, $NHNH_2$, methylamino, dimethylamino, benzoylamino, isobutyrylamino, methoxy, ethoxy and methylthio.

Some examples of analogues of the purine series are, in addition to purine, xanthine, hypoxanthine, adenine, N-methyladenine, N-benzoyladenine, 2-methylthioadenine, 2-aminoadenine, 6-hydroxypurine, 2-amino-6-chloropurine, 2-amino-6-methylthiopurine, guanine, N-isobutyrylguanine. Especially preferred are adenine and guanine, and in a broader aspect of the invention 2-aminoadenine, or the base-proteicted derivatives thereof.

If B in any one of formulae (Ii) to (Xi) and (Ii*) to (Xi*) is a pyrimidine radical or an analogue thereof, it is preferably a uracil, more preferably thymine or cytosine radical or an analogue thereof of formula XII, XIIa, XIIb or XIIc

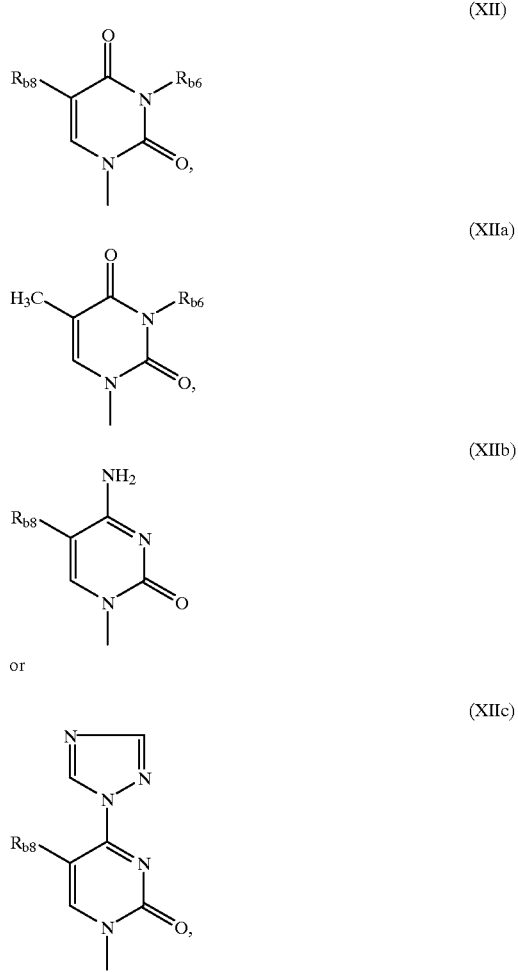

wherein $R_{b6}$ is hydrogen or $C_1$–$C_4$alkyl and $R_{b8}$ is H, OH, SH, $NH_2$, $NHNH_2$, NHOH, NHO-$C_1$–$C_{12}$alkyl, —N=CH—N($C_1$–$C_{12}$alkyl)$_2$, F, Cl, Br, $C_1$–$C_{12}$alkyl, hydroxy-$C_1$–$C_{12}$amino-$C_1$–$C_{12}$alkyl, $C_1$–$C_{12}$alkoxy, benzyloxy or $C_1$–$C_{12}$alkylthio, the hydroxy and amino groups being unsubstituted or substituted by a protecting group, or is phenyl, benzyl, primary amino having from 1 to 20 carbon atoms, secondary amino having from 2 to 30 carbon atoms, $C_1$–$C_{12}$alkenyl or $C_1$–$C_{12}$alkynyl, and the $NH_2$ group in formula XIIb is unsubstituted or substituted by $C_1$–$C_6$alkyl, benzoyl or by a protecting group, and the dihydro derivatives of the radicals of formulae XII, XIIa, XIIb and XIIc.

$R_{b8}$ in formula XII is preferably hydrogen, $C_1$–$C_6$alkcyl or $C_1$–$C_6$hydroxyalkyl, $C_2$–$C_6$alkenyl or $C_2$–$C_6$-alkynyl, F, Cl, Br, $NH_2$, benzoylamino or mono- or di-$C_1$–$C_6$alkylamino.

$R_{b8}$ in formulae XIIb and XIIc is preferably hydrogen, $C_1$–$C_6$alkyl or $C_1$–$C_6$alkoxy or $C_1$–$C_6$-hydroxyalkyl, $C_2$–$C_6$alkenyl or $C_2$–$C_6$alkynyl, F, Cl, Br, $NH_2$, benzoylamino or mono- or di-$C_1$–$C_6$alkylamino.

$R_{b6}$ is preferably hydrogen or methyl. $R_{b8}$ in formula XII is preferably H, F, Cl, Br, $NH_2$, $NHCH_3$, $N(CH_3)_2$, $C_1$–$C_4$alkyl, $C_2$–$C_4$alkenyl or $C_2$–$C_4$alkylamino. $R_{b8}$ in XIIc is preferably hydrogen, $C_1$–$C_4$alkyl, especially methyl, $C_2$–$C_4$alkenyl, especially vinyl, or $C_2$–$C_4$alkyn-1-yl, especially 1-propyn-1-yl, or $NH_2$, $NHCH_3$ or $(CH_3)_2N$.

Some examples of pyrimidine analogues are uracil, thymine, cytohine, 5-fluorouracil, 5-chlorouracil, 5-bromouracil, dihydrouracil, 5-methylcytosine, 5-propynethymine and 5-propynecytosine, thymine, cytosine and 5-methylcytosine being most preferred.

Salts of oligonucleotides or oligonucleotide derivatives according to the invention are especially acid addition salts, salts with bases or, when several salt-forming groups are present, optionally also mixed salts or internal salts.

Salts are especially the pharmaceutically acceptable, non-toxic salts of oligonucleotides or oligonucleotide derivatives as specified above and below (salts that are non-toxic when applied in the correct dose).

Such salts are formed, for example, from the oligonucleotides or oligonucleotide derivatives having an acidic group, for example a carboxy, phosphodiester or phosphorothioate group, and are, for example, their salts with suitable bases, such as non-toxic metal salts derived from metals of groups Ia, Ib, IIa and IIb of the Periodic Table of Elements, especially suitable alkali metal salts, for example lithium, sodium or potassium salts, or alkaline earth metals salts, for example magnesium or calcium salts, furthermore zinc salts or ammonium salts, also those salts that are formed with organic amines, such as unsubstituted or hydroxy-substituted mono-, di- or tri-alkylamines, especially mono-, di- or tri-lower alkylamines, or with quaternary ammonium compounds, for example with N-methyl-N-ethylamine, diethylamine, triethylamine, mono-, bis- or tris-(2-hydroxy-lower alkyl)amines, such as mono-, bis- or tris-(2-hydroxyethyl)amine, 2-hydroxy-tert-butylamine or tris (hydroxymethyl)methylamine, N,N-di-lower alkyl-N-(hydroxy-lower alkyl)-amines, such as N,N-dimethyl-N-(2-hydroxyethyl)-amine or tri-(2-hydroxyethyl)-amine, or N-methyl-D-glucamine, or quaternary ammonium salts, such as tetrabutylammonium salts. The oligonucleotides and their derivatives having, a basic group, for example an amino or imino group, can form acid addition salts, for example with inorganic acids, for example a hydrohalic acid, such as hydrochloric acid, sulfuric acid or phosphoric acid, or with organic carboxylic, sulfonic, sulfo or phospho acids or N-substituted sulfamic acids, such as, for example, acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, also with amino acids, such as, for example, the above-mentioned α-amino icids, and also with methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, 2- or 3-phosphoglycerate, glucose-6-phosphate, N-cyclohexylsulfamic acid (with formation of the cyclamates) or with other acidic organic compounds, such as ascorbic acid. Compounds having acidic and basic groups can also form internal salts. If more than one salt-forming group is present, it is also possible that mixed salts are present.

For the purpose of isolation or purification, it is also possible to use pharmaceutically unacceptable salts.

The terms "oligonucleotides", "oligonucleotide derivatives", "compounds" and "salts" also expressly include individual compounds or individual salts.

The oligonucleotides or oligonucleotide derivatives of the invention have valuable pharmacological properties; thus, they are able to decrease the SAMDC activity in cells by inhibiting the synthesis of this enzyme, and can thus, for example, lower the polyamine levels, especially the spermine and spermidine levels, in cells, showing, for example, antiproliferative activity.

The advantageous pharmacological properties of the oligonucleoticLes or oligonucleotide derivatives according to the invention can be shown, inter alia, by the following experiments:

Using rat liver SAMDC, it can be shown that the compounds of the present invention do not show direct inhibition of isolated SAMDC. To demonstrate this, SAMDC is prepared from SAMDC-deficient *Escherichia coli* which are transfected with an expression plasmid carrying the gene for human SAMDC (see Shantz et al., Biochemistry 31(29), 6848–55 (1992)) and assayed essentially according to known procedures (see Pegg, et al., (1983), in: Tabor et al. (eds.), Methods Enzymol. 94: "Polyamines", Academic Press, New York, p. 234). Aliquots of cell-free dialysed bacterial extracts are stored at −70° C. Assay mixtures for determination of SAMDC activity consist of (final concentrations) 100 mM Tris.HCl pH 7.0, 0.7 mM EDTA, 7.5 mM dithiothreitol, 3.3 mM putrescine, 0.21 mM S-adenosylmethionine (Amersham; 0.1 $\mu$Ci per assay), and variable amounts of SAMDC (specific activity 38±20 nmol.mg$^{-1}$.min$^{-1}$) in a total volume of 150 $\mu$l. Reactions are stopped after incubation for 15 to 60 min at 37° C. by the addition of 0.17 ml 2M HCl and incubated for 20 min at 37° C. $CO_2$ trapped on Whatman 3MM fillers humidified with 25 $\mu$l Soluene-100 (Packard) is counted in a toluene-based liquid szintillation cocktail (®Irgaszint; Ciba-Geigy, Basle, Switzerland). Control assays lacking SAMDC preparation are usually well below 100 cpm. When added to isolated rat liver SAMDC, the antisense oligonucleotides and derivatives thereof according to the invention do not inhibit the enzyme activity. Therefore, effects of these oligonucleotides/their derivatives on cellular SAMDC activity cannot be attributed to a direct SAMDC-inhibitory effect of these molecules.

The SAMDC activity of cell extracts obtained from freeze-thawing of T24 human bladder carcinoma cells in hypotonic buffer is determined after incubation of the cells in the absence or presence of oligonucleotides or their derivatives of the fresent invention according to procedures well-known in the art (see Regenass et al., Cancer Res. 52, 4712–8 (1992)).

Briefly, the following procedure is used: The SAMDC activity of cell extracts obtained by freeze-thawing of cells in hypotonic buffer is determined and the specific SAMDC activity calculated after protein determination with the Bio-Rad protein assay kit (Bio-Rad Laboratories, Richmond, USA—see Bradford, Anal. Biochem. 72, 248–54 (1976). Human T24 bladder carcinoma cells are cultured in Eagle's minimal essential medium (Gibco, Paisley, UK) (see Meyer et al., Int. J. Cancer 43, 851–6 (1989)). When semi-confluent T24 cells are exposed for 6 h to 0.5 $\mu$M antisense oligonucleotides or their derivatives in the presence of an uptake enhancing agent such as 5 $\mu$g/ml ®Lipofectin (a 1:1 (w/w) liposome formulation of the cationic lipid N-[1-(2,3-dioleyloxy)propyl]-N,N,N-trimethylammonium chloride and dioleyl phosphatidylethanolamine (adding up to 1 mg/ml) in membrane filtered water; GIBCO BRL Life Technologies Inc., Gaithersburg, USA) in serum-free medium, the SAMDC antisense oligonucleotides/their derivatives cause a significant reduction of cellular SAMDC activity, preferably resulting in a specific SAMDC activity of 20% or less, most preferably of 10% or less of the specific activity without test compound. In contrast to this, a phosphorothioate oligonucleotide inhibitor complementary to a translation initiation codon region within the UL13 open reading frame of Herpes Simplex Virus (SEQ ID 16 listed below as reference Example; see Crooke et al., Antimicrobial Agents and Chemotherapy 36(3), 527–32 (1992)) shows only weak reduction of SAMDC activity. With this test system it can be shown that the oligonucleotides and their derivatives according to the invention show specificity with regard to the modulation of SAMDC activity.

Employing similar test systems, it can be shown that the oligonuc eotides and especially their derivatives according to the invention inhibit the growth of human T24 bladder carcinoma cells in tissue cultures if 0.5 $\mu$M antisense oligonucleolides or their derivatives in the presence of an uptake enhancing agent such as 5 $\mu$g/ml ®Lipofectin are added to the culture medium.

In order to determine whether the SAMDC modulation by oligonucleotides of the present invention can be correlated with a decrease in the concentration of SAMDC mRNA in T24 cells, Northern blot analysis of SAMDC mRNA is used (for the principles of the assay, see Maniatis et al., "Molecular Cloning—A Laboratory Manual", Cold Spring Harbor Laboratory, New York 1982, p. 383 and following for the aLssay principle). The plasmid pCM9 (see Pajunen et al., J. Biol. Chem. 263(32), 17040–9 (1988)) comprising the human SAMDC cDNA is amplified in *E. coli* HB101. The SAMDC cDNA released from the plasmid by XbaI/SacI digestion is further cleaved into two fragments of each 600 bp in size with EcoR1. The EcoR1/Xba1 fragment is labelled with $\alpha$-[$^{32}$P]-dCTP using random priming and employed for detection of SAMDC mRNA after electrophoretic separation of 10 $\mu$g cellular RNA in glyoxal-agarose gels and transfer to nitrocellulose membranes. Labelled membranes are analysed with a Phosphor-Imager screen (Molecular Dynarnics/Bucher, Basel, Switzerland), and labelling intensity is iltegrated with the laser scanner of the Phosphor-Imager. In T24 cells, mainly the 2.1 kb fragment is detectable, whereas the 3.4 kb transcript is present in trace amounts. Semi-confluent T24 cells are exposed to serum-free medium containing 5 $\mu$g/ml ®Lipofectin without or with an oligonucleotide or its derivative according to the invention in 0.5 $\mu$M concentration or the Herpes Simplex Virus (HSV) phosphorothioate antisense nucleotide according to SEQ ID 16 and Example 16 below (control). After various times (for example after 0 h, 6 h and 24 h), cells are harvested and analysed for SAMDC activity as described above and for SAMDC mRNA content. Loading of equal amounts of RNA is ccntrolled by UV illumination of the gel detecting rRNA and by probing of the membrane with a probe for a house-keeping gene (glutaraldehyde-3-phosphate dehydrogenase=GAPDH). It can be shown that, in contrast to cells incubated in the presence of ®Lipofectin alone or in the presence of (HSV) phosphorothioate antisense nucleotide according to SEQ ID 16 and example 16 below, cells incubated in the presence of an antisense oligonucleotide or its derivative according to the invention show a strong diminution of SAMDC mRNA.

It is well known in the art that depletion of SAMDC activity in cells by direct inhibition at the enzyme level is a promising approach especially for diseases due to cell proliferation, preferably tumor diseases (see Regenass et al., Cancer Res. 52, 4712–8 (1992)).

It is also well known that antisense oligonucleotide derivatives can be taken up into cells in vivo and show favourable pharmacokinetics and biodistributiol (see, for example, Agrawal et al., Proc. Natl. Acad. Sci. USA 88, 7595–9 (1991)).

The compounds of the present invention, due to their ability to diminish the SAMDC activity in cells by modulation of the amount of SAMDC being present in the cells due to modulation of its synthesis, especially inhibition thereof, are therefore effective in the treatment of proliferative and especially hyperproliferative diseases, preferably tumor diseases, especially leukemias; tumors of the prostate, such as prostatic carcinoma; tumors of the colon; brain tumors; hyperproliferative skin and epithelial diseases, for example psoriasis, tumors of the epidermis, such as melanoma; (preferably) lung cancer, such as lung small-cell carcinoma; and/or (most preferably) tumors of the urinary tract, especially bladder carcinoma; and any metastases derived therefrom. The antisense oligonucleotides and their derivatives are able, for example, to cause regression of tumors and to prevent the establishment of metastasis and the growth of micrometastases.

The in vivo antitumor efficacy of the compounds of the present invention can be shown, inter alia, by the following type of experiment: Female Balb/c nude mice (Bomholtgaard, Copenhagen, Denmark) with subcutaneously transplanted T24 human bladder carcinoma cells (see Regenass et al., Cancer Research 54, 3210–3217, (1994)) are treated once daily (day 5–19) by i.v. injection of 6, 0.6 and/or 0.06 mg/kg of a compound of the present invention, dissolved in 0.9% NaCl in water (in 10 ml/kg). With all 3 doses, significant diminution of tumor growth can be found.

The oligonucleotides and oligonucleotide derivatives of the invention can also be used in diagnostics and as research reagents and kits. Since the oligonucltotides and their derivatives of this invention hybridize to the SAMDC gene and its mRNA, sandwich and other assays can easily be constructed to exploit this fact. Furthermore, since the oligonucleotides and their derivatives of this invention hybridize specifically to RNA or DNA sequences relating to particular isozymes of SAMDC and allelic variants of the SAMDC mRNA, such assays can be devised for screening of cells and tissues for particular SAMDC isozymes, also in different animal species. Such assays can be utilized for diagnosis of diseases associated with various SAMDC forms and in different species, preferably the human. Provision of means for detecting hybridization of oligonucleotide with the SAMDC gene can routinely be accomplished. Such provision may include enzyme conjugation, radiolabelling or any other suitable detection systems.

Within the following groups of more preferred embodiments of the invention, more general definitions may be replaced by more specific definitions in accordance with those given above or (especially with regard to definition of pharmaceutical compositions and methods of use) below.

Preferred is an oligonucleotide derivative that is specifically hyblidizable with DNA or RNA, preferably mRNA, deriving from the gene that encodes SAMDC, preferably human SAMDC, comprising analogues of nucleotide units sufficient in number and identity to allow such hybridization, preferably having a length corresponding to 5 to 50 nucleotide units, preferably to 10 to 35 nucleotide units, more preferably to 15 to 22 nucleotide units, and most preferably to 18 to 20 nucleotide units, or a salt of said oligonucleotide derivative where salt-forming groups are present;

or preferably to a pharmaceutical composition that is suitable for administration to a warm-blooded animal, especially man, suffering from a disease that responds to the modulation of SAMDC synthesis, selected from proliferative and e specially hyperproliferative diseases, preferably a tumor disease, especially leukemia, a tumor of the prostate, such as prostatic carcinoma; a tumor of the colon; a brain tumor, a hyperproliferative skin or epithelial disease, for example psoriasis, a tumor of the epidermis, such as melanoma; a (preferably) lung cancer, such as lung small-cell carcinoma; and/or (most preferably) a tumor of the urinary tract, especially bladder carcinoma; and any metastases derived therefrom; comprising an amount of the oligonucleotide derivative, or of a salt thereof if salt-forming groups are present, that is effective in the modulation, preferably inhibition, of the synthesis of SAMDC, preferably in the treatment or prophylaxis of the mentioned diseases, together with at least one pharmaceutically acceptable carrier; and/or to a method of treating the above-mentioned pathological conditions by administration of an oligonucleotide derivative as defined above, preferably in the form of a pharmaceutical composition; and/or to the use of an oligonucleotide derivative for the modulation, preferably inhibition, of SAMDC synthesis in vivo.

More preferred is an oligonucleotide derivative as defined in the last paragraph or an oligonucleotide that is specifically hybridizable with the 3' untranslated region of the mRNA coding for SAMDC (especially human SAMDC), more preferably having a sequence corresponding to that of human SAMDC cDNA, preferably as described in the literature (see Pajunen et al., J. Biol. Chem. 263(32), 17040–9 (1988)); and (in a broader aspect of the invention) an allelic variant thereof, preferably with up to 3 nucleotide analogues that differ in the sequence of a given oligonucleotide derivative or oligonucleotide with respect to the corresponding SAMDC cDNA, more preferably in the sense of conservative mutations, or a salt thereof if salt-forming groups are present.

Even more preferred due to its unexpectedly high effectivity in the test systems described above is an oligonucleotide derivative or (in a broader aspect of thie invention) an allelic variant thereof with up to 3 nucleotide analogues that differ in the sequence of a given oligonucleotide derivative with respect to the corresponding SAMDC cDNA, having a length corresponding to 5 to 50 nucleotide units, preferably to 10 to 35 nucleotide units, more preferably to 15 to 22 nucleotide units, and most preferably to 18 to 20 nucleotide units, or a salt thereof if salt-forming groups are present, being hybridizable to the 3' untranslated region of the SAMDC cDNA (especially human SAMDC cDNA), more preferably a part of the sequence ranging from base position 1060 (5') to 1557 (3') of human cDNA for SAMDC (preferably of the sequence described by Pajunen et al, see above); an oligonucleotide derivative or (in a broader sense) its allelic variant with up to 3 nucleotide analogues that differ in the sequence of a given oligonucleotide derivative with respect to the corresponding SAMDC cDNA, having a length corresponding to 5 to 50 nucleotide units, preferably to 10 to 35 nucleotide units, more preferably to 15 to 22 nucleotide units, and most preferably to 18 to 20 nucleotide units, or a salt thereof if salt-forming groups are present, corresponding to a part of the sequence ranging from base position 1065 to 1105 being most preferred.

Of these compounds, an oligonucleotide derivative corresponding to the sequence described below by SEQ ID NO: 10 or especially by SEQ ID NO: 9 is by far most preferred.

Also very preferred is an oligonucleotide derivative that is specifically hybridizable to the 5' noncoding region of SAMDC mRNA, having a length corresponding to 5 to 50 nucleotide units, preferably to 10 to 35 nucleotide units, more preferably to 15 to 22 nucleotide units, and most preferably to 18 to 20 nucleotide units, and preferably with a sequence that is corresponding to a part of the sequence ranging from base position −248 (5') to −20 (3') of human SAMDC cDNA, more preferably to a part of the sequence ranging from base position −85 to −55, and (in a broader aspect of the invention) an allelic variant thereof, preferably with up to 3 nucleotide analogues that differ in the sequence of a given oligonucleotide derivative with respect to the corresponding SAMDC cDNA, more preferably (as far as the coding region is concerned) in the sznse of conservative mutations. Of these compounds, an oligonucleotide derivative of the sequence described below by SEQ ID NO: 2, or a salt thereof of salt-forming groups are present, is most preferred.

In all of the above-mentioned groups of preferred oligonucleotide derivatives, or salts thereof where salt-forming groups are present, those comprising (preferably containing) at least one building block of formula I or I*, wherein Q is SH, SCH3, F, $N_3$, CN, OCN, $O(CH_2)_zNH_2$ or $O(CH_2)_zCH_3$ where z is from 1 to about 10 or $O(CH_2CH_2O)_vCH_3$ wherein v is from 0 to 12, preferably v is 0 or 1, or Q is also in a broader sense another substituent having similar properties, for example selected from Cl, Br, $CF_3$, $ONO_2$, $NO_2$, $NH_2$ and O—, S— or NH-lower alkyl; and B is a base as defined below; of formula IIa to IIf, IIa* to IIf*, IIIa to IIIh, IIIa* to IIIh*, IVa–IVd, IVa* to IVd*, Va to Vc, Va* to Vc*, VIa to VIb, VIa* to VIb*, VII, VII*, VIII, VIII*, IX, IX*, X or of formula X* given above, wherein B is a base radical as defined below, Q is H, OH, SH, SChh3, F, $N_3$, CN, OCN, $O(CH_2)_zNH_2$ or $O(CH_2)_zCH_3$ where z is from 1 to about 10 or $O(CH_2CH_2O)_vCH_3$ wherein v is from 0 to 12, preferably v is 0 or 1, or Q is also in a broader sense another substituent having similar properties, for example selected from Cl, Br, $CF_3$, $ONO_2$, $NO_2$, $NH_2$ and O—, S— or NH-lower alkyl, most especially hydroxy or preferably hydrogen, and the other moieties have the meanings given behind the respective formula; are even more preferred; and wherein the other building blocks can, in addition to those just mentioned, also comprise building blocks of formula I or I* wherein Q is H or OH and B is a radical of a base selected from adenine, guanine, thymine and cytosine; a nucleotide derivative where no building block of formula I or I*, wherein Q is H or OH and B is a radical of a base selected from adenine, guanine, thymine and cytosine (or a salt thereof where salt-forming groups are present) is present being strongly preferred; and a nucleotide derivative where all building blocks being of the same type with regard to the altered sugar moieties and/or inter-sugar linkages (or a salt thereof where salt-forming groups are present) being the most preferred; a base radical B, if not specified above, being a purine radical or an analogue thereof or a pyrimidine radical or an analogue thereof, preferably a purine radical or an analogue thereof of formula XI, XIa, XIb, XIc, XId, XIe or XIf or a thymine or cytosine radical or an analogue thereof according to formula XII, XIIa, XIIb, XIIc, most preferred being a radical of adenine, guanine, cytosine, 5-methylcytosine or thymine.

In all of the definitions given above, a nucleotide derivative containing only phosphorothioate building blocks of formula Ia and/or IIa*, wherein X is SH and Y is 0 (the central group [O—(P—SH)(=O)—O] being tautomerizable to [O—(P=S)(—OH)—O] with the more stable form depending, among others, on the solvent and the state of ionization) and wherein B and Q have the given meanings, most preferebly B being a radical of adenine, guanine, cytosine or thymine and Q being OH or preferably H, or a salt thereof, is most preferred.

Absolute preference is given to an oligonucleotide derivative given below in the examples, especially a phosphorothioate oligonucleotide derivative corresponding to SEQ ID NO: 10 and more preferably SEQ ID NO: 9; or a pharmaceutically acceptable salt thereof; or an unmodified oligonucleotide of one of these sequences, or a salt thereof.

In any of the groups mentioned above, the oligonucleotide derivative may be free or conjugated, for example to a group forming micelles, to an antibody, a carbohydrate, a receptor-binding group, a steroid, such as cholesterol, a polypeptidc;, an intercalating agent, such as an acridine derivative, a long-chain alkohol, a phospholipid and/or another lipophilic group, or more of these groups which may also be selected independently from each other.

The oligonucleotides and their derivatives in accordance with this invention may be conveniently and routinely made in analogy to or through methods and using starting materials well-known in the art (for reviews, see, inter alia, Milligan et al., J. Med. Chem. 36(14), 1923–37 (1993) and Uhlmann et al., Chemical Rev. 90(4), 543–84 (1990); see International Application WO 92/20823 published Nov. 11, 1992), for example by the well-known technique of solid phase synthesis. Equipment for such synthesis is sold by several vendors including (Applied Biosystems Inc., Foster City, Calif., USA). Any other means for such synthesis may also be employed; the actual synthesis of the oligonucleotides is well within the talents of the routineer. It is also well known to use similar techniques to prepare other oligonucleotides such as the phosphorothioates and nucleoside modified derivatives.

Most preferably, phosphorothioate analogues of the invention can be made by methods known in the art, preferably by reacting a starting material which contains a 5' terminal fragment of the formula XIII,

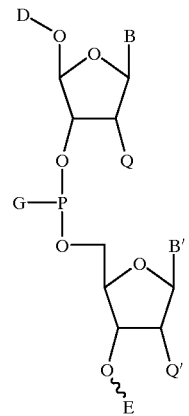

(XIII)

(or a tautomer thereof) wherein D is a hydroxy protecting group or a, B and B' independently represent bases as defined above for B in any one of formulae I to X, Q and Q' independently represent H, OH, SH, SCH3, F, $N_3$, CN, OCN, O)($CH_2$)$_z$$NH_2$ or O($CH_2$)$_z$$CH_3$ where z is from 1 to about 10 or O($CH_2CH_2O$)$_v$$CH_3$ wherein v is from 0 to 12, preferably v is 0 or 1 or Q is also in a broader sense another substituent having similar properties, for example selected from Cl, Br, $CF_3$, $ONO_2$, $NO_2$, $NH_2$ and O—, S— or NH-lower alkyl; G is hydrogen, lower alkoxy or 2-cyanoethoxy and E is a hydroxy protecting group, a carrier or a 3' free or carrier-bonded mono- or oligonucleotide analogue wherein in place of any phosphodiester group {O—[P(=O)(—OH)]—O} a phosphorothioate analogue {O—[P(=S)(—OH)]—O}/{O—[P(—SH)(=O)] or a group of the formula {O—[(P=O)—H]—O}/{O—(P—OH)—O} is present, with a sulfujylating reagent with simultaneous oxidation of any trivalent phosphorus being present, where necessary further functional groups being in protected form, and, where necessary, removing any protecting groups and/or carriers, and, if desired, separating any resulting mixtures of isomers into the individual isomers, and/or transforming a resulting free phosphorothioate oligonucleotide into a salt, and/or transforming a resulting salt into the free form or into a different salt.

In detail, the synthesis is preferably carried out as follows:

Any functional groups being present can be in unprotected or protected form, the protecting groups being selected from those mentioned above for OH or amino/imino groups (SH protecting groups can be selected from those given above for hydroxy groups). A characteristic of these protecting groups is that they are not present in the final products. Protecting groups can be removed by standard methods known in the art, such as those mentioned in the references given above.

D is preferably the dimethoxytrityl group; this group can be removed preferably by acid hydrolysis, for example with mild acids such as formic acid, acetic acid, dichloroacetic acid or furthermore trifluoroacetic acid, in water or organic solvents such as halogenated solvents, for example dichloromethane, cyclic ethers, for example tetrahydrofurane, or lower-alkylcyanides, for example acetonitrile, or mixtures thereof.

It is most preferred that the terminal hydroxy protecting group D in the resulting phosphorothioate oligonucleotide is removed in a step separate from and after the removal of further protecting groups, such as acetyl, benzoyl, phenoxyacetyl, 4-tert-butylphenoxyacetyl, N,N-dimethylformamidinyl, N-methylpyrrolidin-2-yliden, succinyl, 2-cyanoethyl and similar protecting groups that can be removed in a first deprotection step by basic hydrolysis, preferably in the presence of a nitrogen base, such as ethanolamine in an alcohol, such as ethanol, or preferably in the presence of ammonium hydroxide in an aqueous solvent, such as water, at temperatures ranging preferably from about 10 to about 80° C., and then purify the resulting OH-protected oligonucleotide derivative by chromatography on lipophilic adsorbents, such as reverse phase HPLC material, and then, in the purified oligonucleotide derivative, finally removing the OH protecting group, preferably the dimethoxy trityl group, by acid hydrolysis as described above.

B and B' preferably each represent a radical derived from one of the bases adenine, guanine, thymine, cytosine or 5-methylcytosine.

G is preferably 2-cyanoethoxy, the 3' free or carrier-bonded mono- or oligonucleotide analogue then being one wherein, in place of any phosphodiester group {O—[P(=O)(—OH)]—O }, a phosphorothioate analogue {O—[P(=S)(—OH)]—O}/{O—[P(—SH)(=O)] is present.

If G is OH, the 3' free or carrier-bonded mono- or oligonucleotide analogue can be one wherein either in place of any phosphodiester group {O—[P(=O)(—OH)]—O} a phosphorothioate group {O—[P(=S)(—OH)]—O}/{O—[P(—SH)(=O)— two tautomeric forms] is present or one ore more groups of the formula {O—[(P=O)—H]—O}/{O—(P—OH)—O} (two tautomeric forms) are present instead of one or more, maximally all, phosphorothioate bonds. In the latter case, in the process according to the invention all phosphorus atoms in the respective oligonucleotide can be thiolated simultaneously.

E is preferably a 3' free or carrier-bonded mono- or oligonucleotide analogue wherein in place of any phosphodiester group {O—[P(=O)(—OH)]—O} a phosphorothioate analogue {O—[P(=S)(—OH)]—O}/{O—[P(—SH)(=O)] or a group of the formula {O—[(P=O)—H]—O}/{O—(P—OH)—O} (two tautomeric forms) is present.

Where possible, any starting material can also be present in the form of a salt.

A sulfurylating reagent which is capable of reaction with simultaneous oxidation of any trivalent phosphorus being present, is, for example, selected from the group comprising $S_8$ in an organic solvent in the presence of a nitrogen base, such as $S_8$ in pyridine/triethylamine or $S_8$ in 2,6-lutidine; sulfur in $CS_2$ in the presence of a nitrogen base, such as triethylamine or pyridine; 3H-1,2-benzodithiol-3-one-1,1-dioxide in acetonitrile; and most preferably diisopropoxy-thiophosphoric acid disulfide of the formula XIV

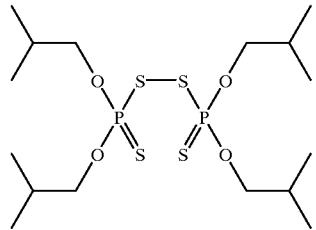

(XIV)

in an organic solvent, such as acetonitrile, in the presence of a tertiary nitrogen base, such as pyridine. The preferred temperatures are in the range from 10 to 80° C., most preferably around room temperature.

The starting material with a fragment according to formula XIII (which makes the respective oligonucleotide complete with respect to the number of nucleotide units) can be synthesized according to methods known in the art, preferably by a combination of standard cyanoethyl phosphoramidite chemistry and simultaneous sulfurylation plus oxidation plus a further step according to standard cyanoethyl amidite chemistry to yield the corresponding triester starting materials (G being lower alkyl or 2-cyanoethyl in formula XIII) or (especially if several phosphodiester groups are present in the starting material of formula XIII due to an appropriate group E corresponding to an oligonucleotide analogue wherein in place of any phosphodiester group a group of the formula {O—[(P=O)—H]—O}/{O—(P—OH)—O} is present) H-phosphonate chemistry (see Uhlmann et al., Chemical Reviews 90(4), 543–84 (1990) for review and further references).

To synthesize oligonucleotide derivatives with one or more building blocks of any one of formulae I and I* to X and X* wherein Q is O($CH_2CH_2O$)$_v$$CH_3$ wherein v has the meanings defined above, and the other moieties are as defined, the respective starting material (either a building block or a complete oligonucleotide or its derivative)

wherein at least one Q is hydroxy can, for example, be reacted in an inert solvent with a compound of formula XV,

X—(CH$_2$—CH$_2$—O)$_v$—CH$_3$     (XV)

wherein X is a leaving group and v is as defined above, functional groups being present in the starting materials being protected by protecting groups as defined above which can be removed at appropriate stages.

A leaving group X may, for example, be halogen, such as Cl, Br or I, Arylsulfonyl, such as 4-toluolsulfonyl, or lower alkane sulfonyl, such as mesyl-sulfonyl.

The reaction is carried out preferably in the presence of a strong base, such as an alkali metal hydride, for example NaH, in an inert solvent, such as an ether, for example a cyclic ether, such as tetrahydrofurane, at temperatures ranging from 30° C. to the boiling point of the reaction mixture, preferably under reflux conditions.

The separating of any resulting mixtures of isomers into the individual isomers can be done according to methods well-known in the art, for example using chromatographic procedures in order to separate diastereomers. Separation at the stage of a starting material or small intermediates is preferred due to possible difficulties in the separation of larger oligonucleotides/oligonucleotide analogues.

The transformation of resulting free compounds into their salts can be achieved according to standard methods, salts of cationic groups for example being available by treatment with appropriate acids or anion exchangers, and salts of anionic groups being available by treatment with an appropriate base or cation exchanger; or preferably by dialysis of the respective compound against a solution of the desired cation.

Salts can be transformed into the free compounds according to standard procedures, metal or ammonium salts for example by treatment with an appropriate acid or an acidic ion exchanger, and acid addition salts by treatment with an appropriate base or basic ion exchanger.

The transfer of salts into different salts is possible in analogy to the transformation of a free compounds into a salt, as mentioned above.

The above-mentioned reactions can be carried out under reaction conditions that are known per se, in the absence or customarily in the presence of solvents or diluents, preferably those solvents and diluents that are inert towards the reagents used and are solvents therefore, in the absence or presence of catalysts, condensation agents or neutralising agents, depending on the nature of the reaction and/or the reactants at reduced, normal or elevated temperature, e.g. in a temperature range of from approximately −80° C. to approximately 250° C., preferably from approximately −20° C. to approximately 150° C., for example from room temperature to the reflux temperature, under atmospheric pressure or in a closed vessel, if desired under pressure, for example at the pressure produced in the reaction mixture under the reaction conditions in a closed tube, and/or in an inert atmosphere, e.g. under an argon or nitrogen atmosphere. The reaction conditions specifically mentioned are preferred.

Solvents and diluents are, for example, water, alcohols, for example lower alkanols, such as methanol, ethanol or propanol, diols, such as ethylene glycol, triols, such as glycerol, or aryl alcohols, such as phenol, acid amides, for example carboxylic acid amides, such as dimethylformamide, dimethylacetamide or 1,3-dimethyl-3,4,5,6-tetrahydro-2(1H)-pyrimidinone (DMPU), or amides of inorganic acids, such as hexamethylphosphoric acid triamide, ethers, for example cyclic ethers, such as tetrahydrofuran or dioxane, or acyclic ethers, such as diethyl ether or ethylene glycol dimethyl ether, halogenated hydrocarbons, such as halo-lower alkanes, for example methylene chloride or chloroform, ketones, such as acetone, nitrites, such as acetonitrile, acid anhydrides, such as acetic anhydride, esters, such as ethyl acetate, bisalkane sulfines, such as dimethyl sulfoxide, nitrogen heterocycles, such as pyridine, hydrocarbons, for example lower alkanes, such as heptane, or aromatic compounds, such as benzene or toluene, or mixtures of those solvents, it being possible to select the particular solvents that are suitable for each cf the above-mentioned reactions.

In view of the close relationship between the oligonucleotides or oligonucleotide derivatives that have the properties according to the invention and the precursors thereof in free form and in the form of salts and/or tautomers, hereinbefore and hereinafter any reference to the free compounds and starting materials or the salts and/or tautomers thereof should be understood as including the corresponding salts or free compounds and/or tautomers, respectively, as appropriate and expedient, provided that the compounds contain one or more salt-forming groups, e.g. basic groups, such as amino or imino groups, and/or acidic groups, such as carboxy, phosphoric acid radicals or sulfo (SO$_3$H), and/or tautomerisable groups. In connection with starting materials, intermediates or final products, any reference made hereinbefore and hereinafter to a substituent, a compound, a tautomer or a salt, or to substituents, compounds, tautomers or salts, is to be understood, irrespective of whether the singular or the plural is used, as meaning "one or more" as appropriate and expedient. Starting materials may also be used in protected fonm, where necessary, appropriate and expedient, it being possible for the protecting groups to be removed at suitable times. Protecting groups, their introduction ancL their removal are especially as defined above.

The compounds, including their salts, may also be obtained in the form of hydrates, or their crystals may include, for example, the solvent used for crystallisation.

In the process of the present invention the starting materials used are preferably those that result in the compounds described at the beginning as being preferred.

The invention relates also to those forms of the process in which a compound obtainable as intermediate at any stage of the process is used as starting material and the remaining process steps are carried out, or in which a starting material is formed under the reaction conditions or is used in the form of a derivative, for example a salt, thereof.

The sequence and reaction conditions of all the described reactions are preferably to be so selected as considered appropriate and expedient to the person skilled in the art.

Pharmaceutical Compositions and Processes:

The present invention relates also to pharmaceutical compositions comprising an oligonucleotide or an oligonucleotide derivative with the properties according to the invention as active ingredient. Especially preferred are compositions for enteral, especially oral, or parenteral administration. The compositions comprise the active ingredient on its own or, preferably, together with a pharmaceutically acceptable carrier. The dose of the active ingredient depends on the disease to be treated, and on the species, age, weight and individual condition, as well as the method of administration.

Preferred is a pharmaceutical composition that is suitable for administration to a warm-blooded animal, especially man, suffering from a disease that responds to the modulation of SAMDC synthesis; for example a proliferative and especially hyperproliferative disease, preferably a tumor disease, especially a leukemia; a tumor of the prostate, such as prostatic carcinoma; a tumor of the colon; a brain tumor; a hyperproliferative skin or epithelial disease, for example psoriasis; a tumor of the epidermis, such as melanoma; (preferably) a lung cancer, such as lung small-cell carcinoma; and/or (most preferably) a tumor of the urinary tract, especially bladder carcinoma; and any metastases derived therefrom; comprising an amount of the active ingredient, or of a salt thereof if salt-forming groups are present, that is effective in the modulation of the synthesis of SAMDC, preferably in the treatment or prophylaxis of the mentioned diseases, together with at least one pharmaceutically acceptable carrier.

The pharmaceutical compositions comprise from approximately 0.0001% to approximately 95% active ingredient, dosage forms that are in single dose form preferably comprising from approximately 0.001% to approximately 20% active ingredient, and dosage forms that are not in single dose form preferably comprising from approximately 0.001% to approximately 10% active ingredient. Unit dose forms, such as dragées, tablets, ampoules or capsules, comprise from approximately 0.0005 mg to approximately 0.5 g of the active ingredient, preferably from 0.005 mg to approximately 20 mg.

The pharmaceutical compositions of the present invention are prepared in a manner known per se, for example by means of conventional mixing, granulating, confectioning, dissolving or lyophilising processes. For example pharmaceutical compositions for oral administration can be obtained by combining the active ingredient with one or more solid carriers, where necessary granulating a resulting mixture and processing the mixture or the granules, if desired or appropriate with the addition of further excipients, to form tablets or dragée cores.

Suitable carriers are especially fillers, such as sugars, e.g. lactose, saccharose, mannitol or sorbitol, cellulose preparations and/or calcium phosphates, e.g. tricalcium phosphate or calcium hydrogen phosphate, and binders, such as starches, e.g. corn, wheat, rice or potato starch, methylcellulose, hydroxypropylmethylcellulose, sodium carboxymethylcellulose and/or polyvinylpyrrolidone, and/or, if desired, disintegrators, such as the above-mentioned starches, and also carboxymethyl starch, crosslinked polyvinylpyrrolidone or alginic acid or a salt thereof, such as sodium alginate. Additional excipients are especially flow conditioners and lubricants, e.g. silicic acid, talc, stearic acid or salts thereof, such as magnesium or calcium stearate, and/or polyethylene glycol, or derivatives thereof.

Dragée cores may be provided with suitable, optionally enteric, coatings, there being used, inter alia, concentrated sugar solutions which may comprise gum arabic, talc, polyvinyl-pyrrolidone, polyethylene glycol and/or titanium dioxide, or coating) solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or dragée coatings, e.g. for identification purposes or to indicate different doses of active ingredient.

Orally administrable pharmaceutical compositions are also dry-filled capsules consisting of gelatin, and also soft sealed capsules consisting of gelatin and a plasticiser, such as glycerol or sorbitol. The dry-filled capsules may contain the active ingredient in the form of granules, for example in admixture with fillers, such as corn starch, binders and/or glidants, such as talcum or magnesium stearate, and, where appropriate, stabilisers. In soft capsules, the active ingredient is preferably dissolved or suspended in suitable liquid excipients, e.g. fatty oils, ®Lauroglycol (Gattefossé S.A., Saint Priest, France), ®Gelucire (Gattefossé S.A., Saint Priest, France) or sesame oil, paraffin oil or liquid polyethylene glycols, such as PEG 300 or 400 (Fluka, Switzerland), or polypropylene glykols, to each of which stabilisers or detergents may also be added.

Other oral forms of administration are, for example, syrups prepared in customary manner that comprise the active ingredient e.g. in suspended form and in a concentration of approximately from 0.001% to 20%, preferably approximately 0.001% to about 2%, or in a similar concentration that provides a suitable single dose when administered, for example, in measures of 5 or 10 ml. Also suitable, for example, are powdered or liquid concentrates for preparing shakes, e.g. in milk. Such concentrates can also be packed in single-dose quantities.

Transdermal Delivery Systems are possible, especially with neutral active ingredients according to the invention. Suitable formulations comprise, for example, about 0.0001% to about 2% by weight of active ingredient. In a preferred aspect, there are provided formulations which comprise about 2% to 99.9999% (or the balance to 100%) of a short chain aliphatic alcohol. Suitable alcohols include ethanol, isopropanol, propylene glycol and glycerol. In a more preferred aspect, these formulations may additionally comprise a flux enhancer. Suitable flux enhancers include, for example, decylmethylsulfoxide, dimethylsufoxide as well as cyclic ketones, lactones, anhydrides and esters. Some of these flux enhancers also increase retention of the active ingredient and thus act to increase the concentration of it in the skin itself. For formulations for direct (local) treatment, such as topical application to the skin, it is preferred to use a flux enhancer which not only maximizes transdermal flux, but increases retention of the active ingredient in the skin. Certain cyclic ketone and lactone enhancers have been reported to increase local retention as well and, thus, comprise a preferred class of enhancers for topical administration of the active ingredient. In formulations for systemic treatment, it is preferable to use a flux enhancer which maximizes flux with a minimal local retention of the active ingredient.

Suitable rectally administrable pharmaceutical compositions are e.g. suppositories that consist of a combination of the active ingredient with a suppository base. Suitable suppository bases are e.g. natural or synthetic triglycerides, paraffin hydrocarbons, polyethylene glycols or higher alkanols.

For parenteral administration (which is preferred) there are suitable, especially, aqueous solutions of an active ingredient in water-soluble form, e.g. in the form of a water-soluble salt, or aqueous injection suspensions that comprise viscosity-increasing substances, e.g. sodium carboxymethylcellulose, sorbitol and/or dextran, and, where appropriate, stabilisers. The active ingredient, where appropriate together with excipients, may also be in the form of a lyophilisate and may be made into a solution prior to parenteral administration by the addition of suitable solvents.

Solutions as used e.g. for parenteral administration may also be used as infusion solutions.

The invention relates also to a method of treating the above-mentioned pathological conditions. For this purpose, an active ingredient of the present invention, or a pharmaceutically acceptable salt thereof, may be administered prophylactically or therapeutically, preferably in an amount that is effective against the mentioned diseases, to a warm-blooded animal, e.g. man, requiring such treatment, preferably in the form of pharmaceutical compositions. The dose of the active ingredient defends on the species of the warm-blooded animal to be treated, its body weight, its age and, individual status, individual pharmacokinetic circumstances, the disease to be treated, and the application route. Preferably, for a body weight of approximately 70 kg a daily dose of from 0.001 mg to 1000 mg, e.g. from approximately 0.01 mg to approximately 100 mg, preferably from approximately 0.05 mg to approximately 50 mg, of the active ingredient is administered.

Further Embodiments of the Invention

The invention also relates to a method of modulating the expression of SAMDC comprising contacting tissues or cells containing the gene with an oligrinucleotide derivative comprising from 5 to 50 nucleotide units, preferably from 10 to 35, most preferably from 18 to 20 nucleotide units, specifically hybridizable with selected DNA or RNA deriving from the SAMDC gene, most preferably the corresponding DNA or mRNA.

The invention also relates to a method of detecting the presence of DNA or RNA which encodes SAMDC in cells or tissues comprising contacting the cells or tissues with an oligonucleotide derivative as defined above, for example comprising from 5 to 50 nucleotide units, that is specifically hybridizable with said DNA or RNA, and detecting if hybridization has occurred.

The invention also relates to a method of diagnosing conditions associated with SAMDC (over)expression comprising contacting cells or tissues or body fluids from an animal suspected of having a condition associated with SAMDC (over)expression, or extracts of such samples, with an oligonucleotide or an oligonucleotide derivative as defined above, (preferably) comprising from 8 to 50 nucleotide units, more preferably from 10 to 35 and most preferably from 18 to 20 nucleotide units), specifically hybridizable with selected DNA or RNA deriving from the gene that encodes SAMDC, most preferably the DNA or mRNA, and determining whether hybridization occurs.

A condition that is associated with SAMDC (over) expression is, for example, any one of the diseases mentioned above that responds to modulation of SAMDC expression.

In all these further embodiments of the invention, the oligonucleotides or their derivatives being described above as preferred are more preferred, oligonucleotides or oligonucleotide derivatives according to SEQ ID NO: 10 and especially SEQ ID NO: 9 being by far most preferred.

When cells or tissues are to be contacted with an oligonucleotide or oligonucleotide derivative according to the invention in vitro, conditions where an uptake enhancing agent is present are preferred or even necessary. Uptake enhancing agents are, for example, liposome formulations, such as ®Lipofectin (a 1:1 (w/w) liposome formulation of the cationic lipid N-[1-(2,3-dioleyloxy)propyl]-N,N,N-trimethylammonium chloride and dioleyl phosphatidylethanolamine (adding up to 1 mg/ml) in membrane filtered water; GIBCO BRL Life Technologies Inc., Gaithersburg, USA); ®Lipofectamine (a 3:1 (w/w) liposome formulation of the polycationic lipid 2,3-dioleyloxy-N-[2-(sperminecarboxyamido)ethyl]-N,N-dimethyl-1-propanaminium trifluoroacetate (DOSPA) and the neutral lipid dioleoyl phosphatidylethanolamine (DOPE) in membrane filtered water (GIBCO BRL, USA); N-[1-(2,3-Dioleoyloxy)-propyl]-N,N,N-trimethylamrroniumsulfate (Boehringer Mannheim GmbH, FRG), which are present preferably in concentrations ranging from about 0.2 to about 20 μg/ml, for example about 5 μg/ml, in the respective in vitro experiments.

EXAMPLES

The following examples illustrate the present invention without being intended to limit the same.

The abbrevation MALDI-TOF MS stands for Matrix Associated Laser Desorption Time-of-Flight Mass Spectrum.

The following oligonucleotide analogues are obtained according to the following procedure:

The oligonucleotide derivatives of examples 1 to 15 and reference example 16 are synthesized on an Applied Biosystems 392 DNA-RNA Synthesizer (Applied Biosystems Inc., Foster City, Calif., USA) using standard cyanoethyl phosphoramidite chemistry without removal of the terminal dimethoxytrityl group. Controlled pore glass is used as the carrier material (Applied Biosystems Inc., Foster City, USA). For phosphorothioate oligonucleotides, the standard oxidation bottle is replaced by a 0.1 M solution of diisopropoxy-thiophoshoric acid disulfide in pyridine/acetonitrile 1:3 (v/v) at ambient temperature for the stepwise thiation of the phosphite linkages. The thiation step is followed by the capping step (acetic anhydride/2,6-lutidine/N-methyrlimidazole 12%/12%/4% (v/v/v) in tetrahydrofurane). The resulting crude olignucleotide is deprotected using 33% aqueous ammonium hydroxide at 55° C. overnight. Subsequent purification involves reverse phase HPLC on a Waters HPLC systeri using a ®Nucleosil $C_{18}$ column (10 μm mean bead diameter, silicagel derivatized with octadecyl silanes, obtaineable from Macherey & Nagel, Düren, FRG) ((eluent: 0.05 M triethylammonium acetate, pH=7.0, containing 10 vol-% acetonitrile, increasing to 45 vol-% within 50 min; length of column: 250 mm; diameter of column: 20 mm; flow rate: 15 ml/min; detection: UV absorption at 254 nm). The 5'-terminal dimethoxytrityl group is then removed by treatment with 80% acetic acid, followed by extraction with diethyl ether. The obtained oligonucleotide is dialysed using a regenerated cellulose dialysis mcembrane with a molecular weight cut-off 1.000 (®Spectra/Por Multiple Dialyzer; Spectrum Medical Industries, Inc., Los Angeles, USA) against 100 mM NaCl (once) and water (twice) and finally lyophilized. The correct molecular weight is confirmed by MALDI-TOF Mass Spectroscopy.

The following examples are obtained (the numbers below the sequences indicating the position of the respective terminal nucleotide analogue on the corresponding human SAMDC cDNA as described by Pajunen et al., J. Biol. Chem. 263(3i2), 17040–9 (1988), with respect to the first nucleotide of the start codon (said cDNA has a total length going from position −248 to position 1557, the coding region for SAMDC having position 1 as first nucleotide of the start codon and position 1005 as last position of the stop codon):

| EXAMPLE | SEQ ID | SEQUENCE | | TARGET |
|---|---|---|---|---|
| 1) | 1 | AATTTTCCCG -173 | GCTTTGTGTG -192 | 5' untranslated |
| 2) | 2 | CCCGCCGCTG -61 | CCGCCGCCGC -80 | 5' untranslated |
| 3) | 3 | CCATCACCGT 4 | GAGACTAGCG -16 | translation initiation codon |
| 4) | 4 | AAAAAATGTG 20 | CAGCTTCCAT 1 | translation initiation codon |
| 5) | 5 | GGTTTGCGTC 79 | GGGCTGCTGC 60 | translated |
| 6) | 6 | TGCTGTTGTT 998 | GCTGCTTCTT 979 | translated |
| 7) | 7 | TTCTTAATCA 1012 | ACTCTGCTGT 993 | stop codon |
| 8) | 8 | AAAGCATCCA 1065 | CCACCTTCTA 1046 | 3' untranslated |
| 9) | 9 | GCCCCCAGCA 1086 | TCGACATCTA 1067 | 3' untranslated |
| 10) | 10 | TTATGGAAAG 1100 | CACTGCCCCC 1081 | 3' untranslated |
| 11) | 11 | GGGCTTTCTG 1127 | CAACTACACA 1108 | 3' untranslated |
| 12) | 12 | ACAGCAAGAG 1242 | TGGCAGAGAA 1223 | 3' untranslated |
| 13) | 13 | AGAAAAGCCT 1380 | TGTCTGTGGG 1361 | 3' untranslated |
| 14) | 14 | AGAGGGTTAG 1413 | GCTGAGGCCA 1394 | 3' untranslated |
| 15) | 15 | GGATGTAAAA 1502 | TTCTGGCAGC 1483 | 3' untranslated |
| Reference Example | 16 | GCCGAGGTCC ATGTCGTACG C | | Herpes Simplex Virus |

All examples (1 to 15 as well as the reference example) are phosphorothioate analogues of the corresponding natural oligo-2'-deoxynucleotides.

Example 17

Solutions for i.v. Administration

The actice ingredient of Example 9 is admixed with 0.9% sodium chloride solution in water under sterile conditions to achieve a concentration of a) 0.6 mg/ml
b) 0.06 mg/ml
c) 0.006 mg/ml of the active ingredient.

What we claim is:

1. An oligonucleotide derivative consisting of a sequence of nucleotides and nucleotide analogues corresponding to a sequence selected from the group consisting of SEQ. ID. NO. 9 and SEQ. ID. NO. 10, said oligonucleotide derivative being complementary to the corresponding sequence of a mRNA deriving from the gene of human SAMDC, said oligonucleotide derivative modulating the biosynthesis of human SAMDC, or a salt of said oligonucleotide derivative where salt-forming groups are present.

2. The oligonucleotide derivative according to claim 1 wherein said sequence of nucleotides and nucleotide analogues correspond to a sequence of SEQ. ID. NO. 9, or a salt of said oligonucleotide derivative where salt-forming groups are present.

* * * * *

UNITED STATES PATENT AND TRADEMARK OFFICE
CERTIFICATE OF CORRECTION

PATENT NO : 6,018,042
DATED: : January 25, 2000
INVENTOR(S) : METT, ET AL.

It is certified that there is an error in the above-identified patent and that said Letters Patent is hereby corrected as shown below:

Claim 2, in column 44, line 2 of said claim should read:

-- wherein said sequence of nucleotides and/or nucleotide ana- --.

Signed and Sealed this

Twenty-seventh Day of March, 2001

Attest:

NICHOLAS P. GODICI

Attesting Officer

Acting Director of the United States Patent and Trademark Office